(12) United States Patent
Simon et al.

(10) Patent No.: US 10,265,523 B2
(45) Date of Patent: *Apr. 23, 2019

(54) NON-INVASIVE TREATMENT OF NEURODEGENERATIVE DISEASES

(71) Applicant: ElectroCore, LLC, Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: Electrocore, Inc., Basking Ridge, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/462,605

(22) Filed: Aug. 19, 2014

(65) Prior Publication Data

US 2014/0357936 A1 Dec. 4, 2014

Related U.S. Application Data

(63) Continuation of application No. 13/005,005, filed on Jan. 12, 2011, now Pat. No. 8,868,177, which is a
(Continued)

(51) Int. Cl.
*A61N 1/36* (2006.01)
*A61N 1/40* (2006.01)
(Continued)

(52) U.S. Cl.
CPC .......... *A61N 1/36025* (2013.01); *A61N 1/40* (2013.01); *A61N 2/002* (2013.01); *A61N 2/006* (2013.01); *A61N 2/02* (2013.01); *A61N 1/36114* (2013.01)

(58) Field of Classification Search
None
See application file for complete search history.

(56) References Cited

U.S. PATENT DOCUMENTS 3,590,810 A 7/1971 Kopecky
4,196,737 A 4/1980 Bevilacqua
(Continued)

FOREIGN PATENT DOCUMENTS

EP 2777764 8/2015
KR 101242190 3/2013
(Continued)

OTHER PUBLICATIONS

Mucida D, Park Y, Kim G, Turovskaya O, Scott I, Kronenberg M, Cheroutre H. Reciprocal TH17 and regulatory T cell differentiation mediated by retinoic acid. Science. Jul. 13, 2007;317(5835):256-60.*

(Continued)

*Primary Examiner* — Ankit D Tejani
(74) *Attorney, Agent, or Firm* — Dentons US LLP

(57) ABSTRACT

The present disclosure includes methods and devices for a non-invasive treatment of a neurodegenerative disease through a delivery of energy to a target nervous tissue, such as a vagus nerve of a patient. Such energy can be applied to the patient to generate an electrical impulse. The electrical impulse can be modulated to increase an activity of an anti-inflammatory cytokine in the patient to inhibit inflammation and treat the neurodegenerative disease. Such stimulation can bring about a reduction of neuro-inflammation in some patients suffering from one or more conditions, such as Alzheimer's Disease, Parkinson's Disease, Multiple Sclerosis, postoperative cognitive dysfunction, or postoperative delirium.

31 Claims, 7 Drawing Sheets

Related U.S. Application Data continuation-in-part of application No. 12/964,050, filed on Dec. 9, 2010, now abandoned, which is a continuation-in-part of application No. 12/859,568, filed on Aug. 19, 2010, now Pat. No. 9,037,247, which is a continuation-in-part of application No. 12/408,131, filed on Mar. 20, 2009, now Pat. No. 8,812,112.

(60) Provisional application No. 61/415,469, filed on Nov. 19, 2010.

(51) Int. Cl.
*A61N 2/00* (2006.01)
*A61N 2/02* (2006.01)

(56) References Cited

U.S. PATENT DOCUMENTS

| | | | |
|---|---|---|---|
| 5,458,141 A | 10/1995 | Neil | |
| 5,782,874 A | 7/1998 | Loos | |
| 5,899,922 A | 5/1999 | Loos | |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 7,734,340 B2 | 6/2010 | De Ridder | |
| 7,797,041 B2 | 9/2010 | Libbus et al. | |
| 8,868,177 B2* | 10/2014 | Simon | A61N 1/40 600/9 |
| 2002/0099417 A1 | 7/2002 | Naritoku et al. | |
| 2002/0183237 A1 | 12/2002 | Puskas | |
| 2003/0212311 A1 | 11/2003 | Nova et al. | |
| 2004/0073271 A1 | 4/2004 | Harry et al. | |
| 2004/0122281 A1* | 6/2004 | Fischell | A61N 2/02 600/13 |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0125044 A1* | 6/2005 | Tracey | A61K 31/44 607/45 |
| 2005/0137644 A1 | 6/2005 | Boveja et al. | |
| 2005/0187590 A1 | 8/2005 | Boveja et al. | |
| 2005/0216062 A1 | 9/2005 | Herbst | |
| 2006/0074284 A1 | 4/2006 | Juola et al. | |
| 2006/0074450 A1 | 4/2006 | Boveja et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0038264 A1 | 2/2007 | Jaax et al. | |
| 2007/0067002 A1* | 3/2007 | Lozano | A61N 1/0551 607/45 |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0276449 A1* | 11/2007 | Gunter | A61N 1/36021 607/46 |
| 2008/0006281 A1* | 1/2008 | Sih | A61M 37/00 128/899 |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0077192 A1* | 3/2008 | Harry | A61H 23/0263 607/48 |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0249439 A1* | 10/2008 | Tracey | A61H 39/04 601/46 |
| 2008/0306325 A1 | 12/2008 | Burnett et al. | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0245486 A1 | 9/2013 | Simon et al. | |
| 2014/0005743 A1 | 1/2014 | Giuffrida et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| WO | WO 1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO 2009/021080 | 2/2009 |
| WO | WO 2009/135693 | 11/2009 |
| WO | WO2013066135 | 5/2013 |

OTHER PUBLICATIONS

Nozaki Y, Yamagata T, Sugiyama M, Ikoma S, Kinoshita K, Funauchi M. Anti-inflammatory effect of all-trans-retinoic acid in inflammatory arthritis. Clin Immunol. Jun. 2006;119(3):272-9.*

Pavlov VA, Wang H, Cruza CJ, Friedman SG, Tracey KJ. The cholinergic anti-inflammatory pathway: a missing link in neuroimmunomodulation. Mol Med. May-Aug. 2003;9(5-8):125-34.*

Greicius et al., Functional connectivity in the resting brain: A network analysis of the default mode hypothesis, PNAS, Jan. 2003, vol. 100, No. 1, pp. 253-258.

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

(56) References Cited

OTHER PUBLICATIONS

International Search Report and Written Opinion dated Aug. 25, 2015 in related Application No. PCT/US15/31847 filed May 20, 2015 (10 pages).
Europe Office Action dated Apr. 24, 2018 in related Application No. 15796247.3 filed May 20, 2015 (6 pages).
KR101242190 dated Mar. 25, 2013, Espacenet computer generated English translation (11 pages).
Europe Office Action dated Jul. 26, 2018 in related Application No. 11818591.7 filed Aug. 12, 2011 (8 pages).

* cited by examiner

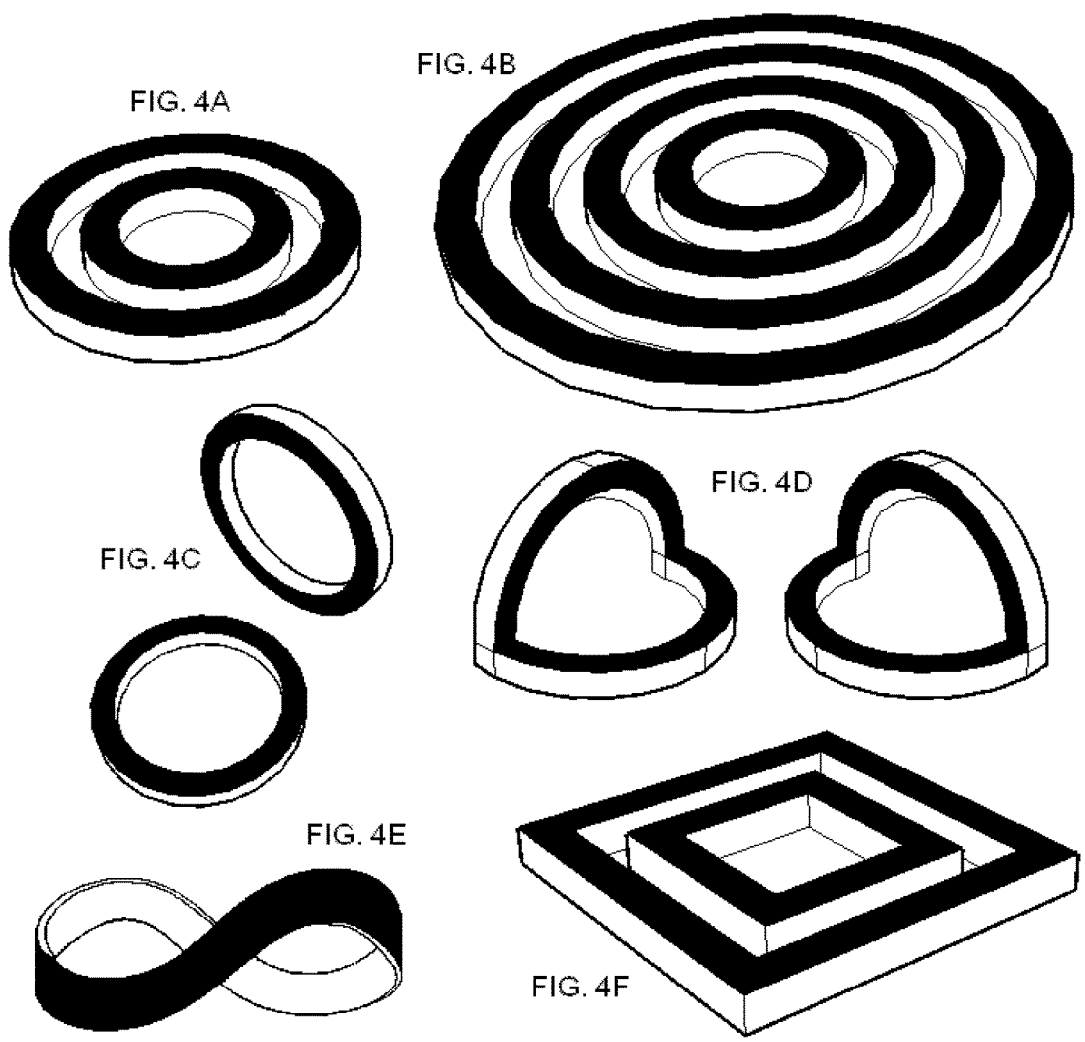

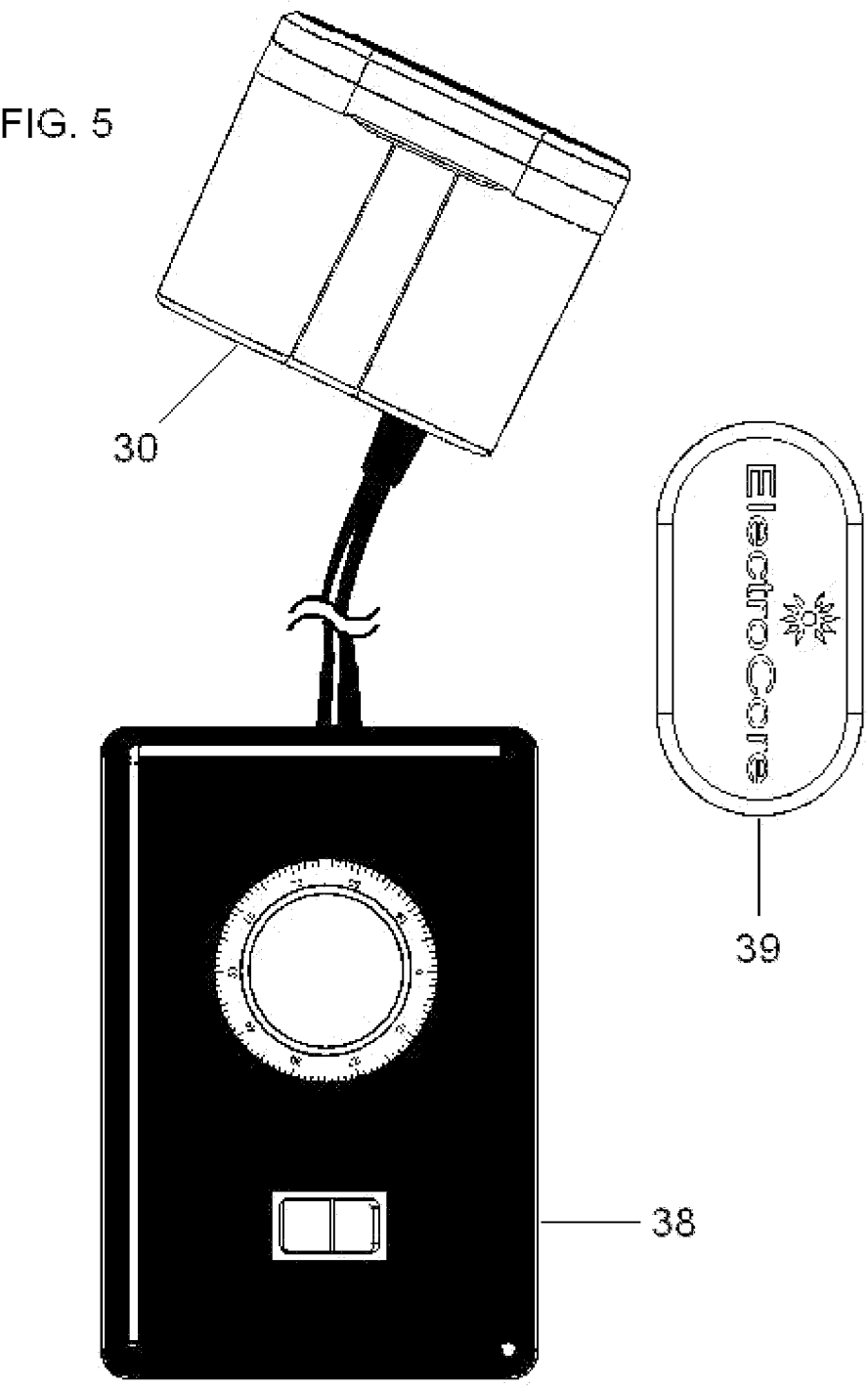

NON-INVASIVE TREATMENT OF NEURODEGENERATIVE DISEASES

CROSS REFERENCE TO RELATED APPLICATIONS

This application is a continuation of Ser. No. 13/005,005 filed Jan. 12, 2011, which is (a) a continuation-in-part of U.S. patent application Ser. No. 12/964,050 filed Dec. 19, 2010, which claims the benefit of priority of U.S. Provisional Patent Application No. 61/415,469 filed Nov. 19, 2010, and (b) a continuation-in-part application of U.S. patent application Ser. No. 12/859,568 filed Aug. 9, 2010, which is a continuation-in-part of U.S. patent application Ser. No. 12/408,131 filed Mar. 20, 2009; each of which is incorporated herein by reference in its entirety.

BACKGROUND OF THE INVENTION

The field of the present invention relates to the delivery of energy impulses (and/or fields) to bodily tissues for therapeutic purposes. It relates more specifically to the use of non-invasive methods and devices, particularly methods that make use of magnetic stimulation devices, to treat neurodegenerative disorders, using energy that is delivered by such devices. The medical disorders include Alzheimer's disease, Parkinson's disease, multiple sclerosis, postoperative cognitive dysfunction, and postoperative delirium. The treatment relates to stimulation of the vagus nerve to reduce neuro-inflammation, wherein pathways involving anti-inflammatory cytokines, the retinoic acid signaling system, and/or neurotrophic factors are enhanced, and/or pathways involving pro-inflammatory cytokines are inhibited.

Treatments for various infirmities sometime require the destruction of otherwise healthy tissue in order to produce a beneficial effect. Malfunctioning tissue is identified and then lesioned or otherwise compromised in order to produce a beneficial outcome, rather than attempting to repair the tissue to its normal functionality. A variety of techniques and mechanisms have been designed to produce focused lesions directly in target nerve tissue, but collateral damage is inevitable.

Other treatments for malfunctioning tissue can be medicinal in nature, but in many cases the patients become dependent upon artificially synthesized chemicals. In many cases, these medicinal approaches have side effects that are either unknown or quite significant. Unfortunately, the beneficial outcomes of surgery and medicines are often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

Nerve stimulation is thought to be accomplished directly or indirectly by depolarizing a nerve membrane, causing the discharge of an action potential; or by hyperpolarization of a nerve membrane, preventing the discharge of an action potential. Such stimulation may occur after electrical energy, or also other forms of energy, are transmitted to the vicinity of a nerve [F. RATTAY. The basic mechanism for the electrical stimulation of the nervous system. Neuroscience Vol. 89, No. 2, pp. 335-346, 1999; Thomas HEIMBURG and Andrew D. Jackson. On soliton propagation in biomembranes and nerves. PNAS vol. 102 (no. 28, Jul. 12, 2005): 9790-9795]. Nerve stimulation may be measured directly as an increase, decrease, or modulation of the activity of nerve fibers, or it may be inferred from the physiological effects that follow the transmission of energy to the nerve fibers.

Electrical stimulation of the brain with implanted electrodes has been approved for use in the treatment of various conditions, including movement disorders such as essential tremor and Parkinson's disease. The principle underlying these approaches involves disruption and modulation of hyperactive neuronal circuit transmission at specific sites in the brain. Unlike potentially dangerous lesioning procedures in which aberrant portions of the brain are physically destroyed, electrical stimulation is achieved by implanting electrodes at these sites. The electrodes are used first to sense aberrant electrical signals and then to send electrical pulses to locally disrupt pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure requires penetrating the skull, and inserting an electrode into brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted, and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neuro-vasculature.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

Yet another application of electrical stimulation of nerves has been the treatment of epilepsy and depression by vagus nerve stimulation (VNS) [U.S. Pat. No. 4,702,254 entitled Neurocybernetic prosthesis, to ZABARA; U56341236 entitled Vagal nerve stimulation techniques for treatment of epileptic seizures, to OSORIO et al; US5299569 entitled Treatment of neuropsychiatric disorders by nerve stimulation, to WERNICKE et al]. For this procedure, the left vagus nerve is ordinarily stimulated at a location on the neck by first implanting an electrode there, then connecting the electrode to an electrical stimulator.

Despite the clinical success of VNS in treating epilepsy and depression, a specific mechanism underlying VNS relief of symptoms is not currently known. Vagus afferent fibers innervate several medullary structures; with the nucleus of the tractus solitarius (NTS) receiving bilateral inputs totaling approximately eighty percent of all vagal afferents. The NTS has widespread projections, including direct or multiple synaptic projections to the parabrachial nucleus, vermis, inferior cerebellar hemispheres, raphe nuclei, periaquaductal gray, locus coeruleus, thalamus, hypothalamus, amygdala, nucleus accumbens, anterior insula, infralimbic cortex, and lateral prefrontal cortex, making it difficult to determine the area or neuronal pathway mediating VNS effects. However, functional imaging studies have concluded that VNS may bring about changes in several areas of the brain, including the thalamus, cerebellum, orbitofrontal cortex, limbic system, hypothalamus, and medulla. The stimulation of particular areas of the brain has been suggested as a mechanism for the effects of VNS, but such localized stimulation of the brain may depend upon the parameters of the stimulation (current, frequency, pulse width, duty cycle, etc.). Those parameters may also determine which neurotransmitters are modulated (including norepinephrine, seratonin, and GABA) [Mark S. George, Ziad Nahas, Daryl E. Bohning, Qiwen Mu, F. Andrew Kozel, Jeffrey Borckhardt, Stewart Denslow. Mechanisms of action of vagus nerve stimulation (VNS). Clinical Neuroscience Research 4 (2004) 71-79; Jeong-Ho Chae, Ziad Nahas, Mikhail Lomarev, Stewart Denslow, Jeffrey P. Lorberbaum, Daryl E. Bohning, Mark S. George. A review of functional neuroimaging studies of vagus nerve stimulation (VNS). Journal of Psychiatric Research 37 (2003) 443-455; G. C. Albert, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES DA, Brown V J. Vagal nerve stimulation: a review of its applications and potential mechanisms that mediate its clinical effects. Neurosci Biobehav Rev (2005) 29:493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4].

To date, the selection of stimulation parameters for VNS has been highly empirical, in which the parameters are varied about some initially successful set of parameters, in an effort to find an improved set of parameters for each patient. A more efficient approach to selecting stimulation parameters might be to select a stimulation waveform that mimics electrical activity in the region of the brain that one is attempting to stimulate, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al.

The present disclosure involves devices and medical procedures that stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin. Both TENS and percutaneous electrical stimulation can be to some extent unpleasant or painful, in the experience of patients that undergo such procedures. In the case of TENS, as the depth of penetration of the stimulus under the skin is increased, any pain will generally begin or increase.

Neurodegenerative diseases result from the deterioration of neurons, causing brain dysfunction. The diseases are loosely divided into two groups—conditions affecting memory that are ordinarily related to dementia and conditions causing problems with movements. The most widely known neurodegenerative diseases include Alzheimer (or Alzheimer's) disease and its precursor mild cognitive impairment (MCI), Parkinson's disease (including Parkinson's disease dementia), and multiple sclerosis.

Less well-known neurodegenerative diseases include adrenoleukodystrophy, AIDS dementia complex, Alexander disease, Alper's disease, amyotrophic lateral sclerosis (ALS), ataxia telangiectasia, Batten disease, bovine spongiform encephalopathy, Canavan disease, cerebral amyloid angiopathy, cerebellar ataxia, Cockayne syndrome, corticobasal degeneration, Creutzfeldt-Jakob disease, diffuse myelinoclastic sclerosis, fatal familial insomnia, Fazio-Londe disease, Friedreich's ataxia, frontotemporal dementia or lobar degeneration, hereditary spastic paraplegia, Huntington disease, Kennedy's disease, Krabbe disease, Lewy body dementia, Lyme disease, Machado-Joseph disease, motor neuron disease, Multiple systems atrophy, neuroacanthocytosis, Niemann-Pick disease, Pelizaeus-Merzbacher Disease, Pick's disease, primary lateral sclerosis including its juvenile form, progressive bulbar palsy, progressive supranuclear palsy, Refsum's disease including its infantile form, Sandhoff disease, Schilder's disease, spinal muscular atrophy, spinocerebellar ataxia, Steele-Richardson-Olszewski disease, subacute combined degeneration of the spinal cord, survival motor neuron spinal muscular atrophy, Tabes dorsalis, Tay-Sachs disease, toxic encephalopathy, transmissible spongiform encephalopathy, Vascular dementia, and X-linked spinal muscular atrophy, as well as idiopathic or cryptogenic diseases as follows: synucleinopathy, progranulinopathy, tauopathy, amyloid disease, prion disease, protein aggregation disease, and movement disorder. A more comprehensive listing may be found at the web site (www) of the National Institute of Neurological Disorders and Stroke (ninds) of the National Institutes of Health (nih) of the United States government (gov) in a subdirectory (/disorder/disorder_index) web page (htm). It is understood that such diseases often go by more than one name and that a nosology may oversimplify pathologies that occur in combination or that are not archetypical.

Certain other disorders, such as postoperative cognitive dysfunction have been described only recently, and they too may involve neuro-degeneration. Other disorders such as epilepsy may not be primarily neurodegenerative, but at some point in their progression they might involve nerve degeneration.

Despite the fact that at least some aspect of the pathology of each of the neurodegenerative diseases mentioned above is different from the other diseases, their pathologies ordinarily share other features, so that they may be considered as a group. Furthermore, aspects of their pathologies that they have in common often make it possible to treat them with similar therapeutic methods. Thus, many publications describe features that neurodegenerative diseases have in common [Dale E. Bredesen, Rammohan V. Rao and Patrick Mehlen. Cell death in the nervous system. Nature 443 (2006): 796-802; Christian Haass. Initiation and propagation of neurodegeneration. Nature Medicine 16(11, 2010): 1201-1204; Eng H Lo. Degeneration and repair in central nervous system disease. Nature Medicine 16(11, 2010):1205-1209; Daniel M. Skovronsky, Virginia M.-Y. Lee, and John Q. Trojanowski. Neurodegenerative Diseases: New Concepts of Pathogenesis and Their Therapeutic Implications. Annu. Rev. Pathol. Mech. Dis. 1 (2006): 151-70; Michael T. Lin and M. Flint Beal. Mitochondrial dysfunction and oxidative stress in neurodegenerative diseases. Nature 443 (2006): 787-795; Jorge J. Palop, Jeannie Chin and Lennart Mucke. A network dysfunction perspective on neurodegenerative diseases. Nature 443 (2006): 768-773; David C. Rubinsztein. The roles of intracellular protein-degradation pathways in neurodegeneration. Nature 443 (2006): 780-786].

One such common feature is the presence of inflammation, wherein the body recognizes the abnormality of the relevant neuronal tissue and responds to minimize or repair the effects of the abnormality and/or eventually destroy the abnormal tissue. [Sandra Amor, Fabiola Puentes, David Baker and Paul van der Valk. Inflammation in neurodegenerative diseases. Immunology, 129 (2010), 154-169; Mark H. DeLegge. Neurodegeneration and Inflammation. Nutrition in Clinical Practice 23 (2008):35-41; Tamy C Frank-Cannon, Laura T Alto, Fiona E McAlpine and Malù G Tansey. Does neuroinflammation fan the flame in neurodegenerative diseases? Molecular Neurodegeneration 2009, 4:47-59; Christopher K. Glass, Kaoru Saijo, Beate Winner, Maria Carolina Marchetto, and Fred H. Gage. Mechanisms Underlying Inflammation in Neurodegeneration. Cell 140 (2010): 918-934; V. Hugh Perry. The influence of systemic inflammation on inflammation in the brain: implications for chronic neurodegenerative disease. Brain, Behavior, and Immunity 18 (2004): 407-413; Marianne Schultzberg, Catharina Lindberg, Åsa Forslin Aronsson, Erik Hjorth, Stefan D. Spulber, Mircea Oprica. Inflammation in the nervous system—Physiological and pathophysiological aspects. Physiology & Behavior 92 (2007) 121-128; Frauke Zipp and Orhan Aktas. The brain as a target of inflammation: common pathways link inflammatory and neurodegenerative diseases. Trends in Neurosciences 29 (9, 2006) 518-527]. It is understood that inflammation may accompany not only neurodegenerative disease, but also brain injury that is caused, for example, by trauma, stroke, or infection. Consequently, the methods that are disclosed herein may also be applicable to any situation in which inflammation in the central nervous system presents a danger to the patient.

Because excessive and prolonged inflammation may destroy nervous tissue that is associated with neurodegenerative diseases, therapies have been proposed to prevent, reduce, or eliminate the immune response in such inflammation, or to repair damage that may have been produced by inflammation. Inflammation is modulated by cytokines, which are small cell-signaling protein or peptide molecules that are secreted by glial cells of the nervous system, by numerous cells of the immune system, and by many other cell types. Some cytokines may regarded as hormones, but in what follows, the term cytokine is used to refer to any of those immuno-modulating molecules, with the understanding that they may also participate in pathways other than immunomodulation.

In general, one may adopt two approaches to reduce or prevent inflammation that is modulated by cytokines. First, one may attempt to inhibit the release or effectiveness of cytokines that promote inflammation. Those cytokines are called pro-inflammatory, and the first approach is essentially an anti-pro-inflammatory strategy. Because pro-inflammatory cytokines may promote the release of other pro-inflammatory cytokines, the goal is especially to inhibit the release of the initially released pro-inflammatory cytokines in an inflammatory cascade. For example, the cytokine tumor necrosis factor (TNF-alpha) is considered to be a pro-inflammatory cytokine of central importance, and anti-TNF-alpha strategies seek to inhibit the release or effectiveness of TNF-alpha that is released from immune and other cells [Ian A. Clark, Lisa M. Alleva, Bryce Vissel. The roles of TNF in brain dysfunction and disease. Pharmacology & Therapeutics 128 (2010): 519-548; Melissa K McCoy and Malù G Tansey. TNF signaling inhibition in the CNS: implications for normal brain function and neurodegenerative disease. Journal of Neuroinflammation 2008, 5:45].

A second approach to reducing inflammation that is modulated by cytokines is to enhance and/or stimulate the release or effectiveness of cytokines that inhibit inflammation. Those cytokines are called anti-inflammatory, and the second approach is essentially a pro-anti-inflammatory strategy. As indicated below, pro-anti-inflammatory mechanisms are often associated with the repair of tissue, which may correspond in the adult to mechanisms that were used in the embryo to create tissue originally. The cytokine transforming growth factor beta (TGF-beta) is often regarded as anti-inflammatory, but as described presently, its anti-inflammatory capabilities are contingent upon certain conditions being met. According to the second approach, one endeavors to promote such conditions, as well as to promote the release of, for example, TGF-beta into a potentially inflammatory environment.

In a series of publications, patents, and patent applications, Kevin J. TRACEY and colleagues described electrical stimulation of the vagus nerve in an attempt to effect the first, anti-pro-inflammatory strategy [Kevin J. Tracey. The inflammatory reflex. Nature 420 (2002): 853-859; Kevin J. Tracey. Physiology and immunology of the cholinergic anti-inflammatory pathway. J. Clin. Invest. 117 (2007): 289-296; Kevin J. Tracey. Understanding immunity requires more than immunology. Nature Immunology 11 (2010): 561-564; G. R. Johnston and N. R. Webster. Cytokines and the immunomodulatory function of the vagus nerve. British Journal of Anaesthesia 102(4, 2009): 453-462]. U.S. Pat. No. 6,610,713 and U.S. Pat. No. 6,838,471, entitled Inhibition of inflammatory cytokine production by cholinergic agonists and vagus nerve stimulation, to TRACEY, mention treatment of neurodegenerative diseases within a long list of diseases, in connection with the treatment of inflammation through stimulation of the vagus nerve. According to those patents, "Inflammation and other deleterious conditions . . . are often induced by proinflammatory cytokines, such as tumor necrosis factor (TNF; also known as TNF.alpha. or cachectin) . . . " The patents go on to state that "Proinflammatory cytokines are to be distinguished from anti-inflammatory cytokines, . . . , which are not mediators of inflammation." It is clear from those patents that the objective of TRACEY and colleagues is only to suppress the release of proinflammatory cytokines, such as TNF-alpha. There is no mention or suggestion that the method is intended to modulate the activity of anti-inflammatory cytokines, and in fact, the text quoted above disclaims a role for anti-inflammatory cytokines as mediators of inflammation. Those patents and applications make a generally unjustified dichotomy between pro- and anti-inflammatory cytokines, by suggesting that a cytokine could be one or the other, but not both. In particular, the patents make no mention of the cytokine TGF-beta, and there is no suggestion that the role of a cytokine in regards to its pro- or anti-inflammation competence may be inherently indeterminate or indefinite unless more information is provided about the presumed physiological environment in which the cytokine finds itself.

Treatment of neurodegenerative diseases is also mentioned within long lists of diseases in the following related applications to TRACEY and his colleague HUSTON, wherein stimulation of the vagus nerve is intended to suppress the release of proinflammatory cytokines such as TNF-alpha: US20060178703, entitled Treating inflammatory disorders by electrical vagus nerve stimulation, to HUSTON et al.; US20050125044, entitled Inhibition of inflammatory cytokine production by cholinergic agonists and vagus nerve stimulation, to TRACEY; US20080249439, entitled Treatment of inflammation by non-invasive stimulation to TRACEY et al.; US20090143831, entitled Treating inflammatory disorders by stimulation of the cholinergic anti-inflammatory pathway, to HUSTON et al; US 20090248097, entitled Inhibition of inflammatory cytokine production by cholinergic agonists and vagus nerve stimulation, to TRACEY et al. The same observations made above in connection with U.S. Pat. No. 6,610,713 and U.S. Pat. No. 6,838,471 apply to those applications as well.

SUMMARY OF THE INVENTION

The present invention discloses methods and devices for the non-invasive treatment of neurodegenerative conditions, utilizing an energy source that transmits energy non-invasively to nervous tissue. In particular, the devices can transmit energy to, or in close proximity to, a vagus nerve of the patient, in order to temporarily stimulate, block and/or modulate electrophysiological signals in that nerve. The neurodegenerative conditions, disorders or diseases that can be treated with the present invention include Alzheimer's disease, Parkinson's disease, multiple sclerosis, postoperative cognitive dysfunction or postoperative delirium.

In one aspect of the invention, a method for treating a neurodegenerative disorder in a patient comprises applying energy transcutaneously through an outer skin surface of the patient to generate an electrical impulse at or near a selected nerve, such as the vagus nerve, within the patient. The electrical impulse is sufficient to inhibit inflammation in the patient and treat the neurodegenerative disorder. In some embodiments, the electrical impulse is sufficient to inhibit and/or block the release of pro-inflammatory cytokines, such as TNF-alpha. In other embodiments, the electrical impulse is sufficient to increase the anti-inflammatory competence of certain cytokines to thereby offset or reduce the effect of pro-inflammatory cytokines.

In one embodiment, an electrical current is transcutaneously applied through the outer skin surface of the patient to the vagus nerve. In another embodiment, a magnetic field is generated exterior to the patient that is sufficient to induce an electrical impulse at or near the selected nerve (e.g., the vagus nerve) within the patient.

In a preferred embodiment, a time-varying magnetic field is generated within an enclosed coil outside of the patient that induces an electrical field. The electrical field is shaped such that an electrical current is conducted through the outer skin surface of the patient to modulate the selected nerve. The electrical field may be shaped by generating a second time-varying magnetic field within a second enclosed coil positioned near or adjacent to the first enclosed coil. In other embodiments, the electrical field may be shaped by positioning a conducting medium around a portion of the enclosed coil such that the direction of the electrical field is constrained within the conducting medium.

In another aspect of the invention, an apparatus for applying energy transcutaneously to a target region within a patient with a neurodegenerative disorder is provided. The apparatus includes a source of energy for generating an energy field that is located essentially entirely exterior to an outer skin surface of the patient. The energy field is sufficient to transcutaneously pass through the outer skin surface and generate an electrical impulse at or near the target region. The electrical impulse modulates activity of a selected nerve at the target region to inhibit inflammation in the patient and treat the neurodegenerative disorder. The apparatus preferably also includes a conduction medium that electrically couples the electric field with the outer skin surface to facilitate passage of the electric current therethrough.

In an exemplary embodiment, a magnetic stimulator is used to modulate electrical activity of the vagus nerve. The stimulator comprises a source of electrical power, a magnetically permeable toroidal core, and a coil that is wound around the core. The device also comprises a continuous electrically conducting medium with which the coil and core are in contact, wherein the conducting medium has a shape that conforms to the contour of a target body surface of a patient when the medium is applied to the target body surface. For the present medical applications, the device is ordinarily applied to the patient's neck. The source of power supplies a pulse of electric charge to the coil, such that the coil induces an electric current and/or an electric field within the patient. The stimulator is configured to induce a peak pulse voltage sufficient to produce an electric field in the vicinity of a nerve such as the vagus, to cause the nerve to depolarize and reach a threshold for action potential propagation. By way of example, the threshold electric field for stimulation of nerve terminals may be about 8 V/m at 1000 Hz. For example, the device may induce an electric field within the patient of about 10 to 600 V/m and an electrical field with a gradient of greater than 2 V/m/mm.

The preferred magnetic stimulator comprises two toroidal coils and corresponding cores that lie side-by-side, each containing a high-permeability material, wherein current passing through a coil produces a magnetic field within the core of about 0.1 to 2 Tesla. Current passing through a coil may be about 0.5 to 20 amperes, typically 2 amperes, with voltages across each coil of 10 to 100 volts. The current is passed through the coils in bursts of pulses. The burst repeats at 1 Hz to 5000 Hz, preferably at 15-50 Hz. The pulses have duration of 20 to 1000 microseconds, preferably 200 microseconds and there may be 1 to 20 pulses per burst. The preferred magnetic stimulator shapes an elongated electric field of effect that can be oriented parallel to a long nerve, such as the vagus nerve.

By selecting a suitable waveform to stimulate the nerve, the magnetic stimulator produces a correspondingly selective physiological response in an individual patient. In general, the induced electrical signal has a frequency between about 1 Hz to 3000 Hz and a pulse duration of between about 10-1000 microseconds. By way of example, at least one induced electrical signal may be of a frequency between about 15 Hz to 35 Hz. By way of example, at least one induced electrical signal may have a pulsed on-time of between about 50 to 1000 microseconds, such as between about 100 to 300 microseconds. The induced electrical signal may have any desired waveform, which may comprise one or more of: a full or partial sinusoid, a square wave, a rectangular wave, and triangle wave.

Teachings of the present invention demonstrate how non-invasive stimulators may be positioned and used against body surfaces, particularly at a location on the patient's neck under which the vagus nerve is situated. Those teachings also provide methods for treatment of particular neurodegenerative diseases that involve neurodegeneration, neuroinflammation, or inflammation more generally. However, it should be understood that application of the methods and devices is not limited to the examples that are given.

Stimulation of the vagus nerve with the magnetic stimulator brings about reduction of neuroinflammation in patients suffering from conditions comprising Alzheimer's Disease, Parkinson's Disease, Multiple Sclerosis, postoperative cognitive dysfunction and postoperative delirium. The reduction in inflammation is effected by enhancing the anti-inflammatory competence of cytokines such as TGF-beta, wherein a retinoid or components of the retinoic acid signaling system provide an anti-inflammatory bias; by enhancing anti-inflammatory activity of a neurotrophic factor such as NGF, GDNF, BDNF, or MANF; and/or by inhibiting the activity of pro-inflammatory cytokines such as TNF-alpha.

The novel systems, devices and methods for treating medical conditions using the disclosed magnetic stimulator or other non-invasive stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIGS. 4A-4F illustrate different embodiments showing the geometry of the toroidal core materials around which coils of wire may be wound in an embodiment of the present disclosure.

FIG. 5 illustrates the housing and cap of the dual-toroid magnetic stimulator coils of FIG. 3, attached via cable to a box containing the device's impulse generator, control unit, and power source.

DETAILED DESCRIPTION OF THE PREFERRED EMBODIMENTS

Figure 1:
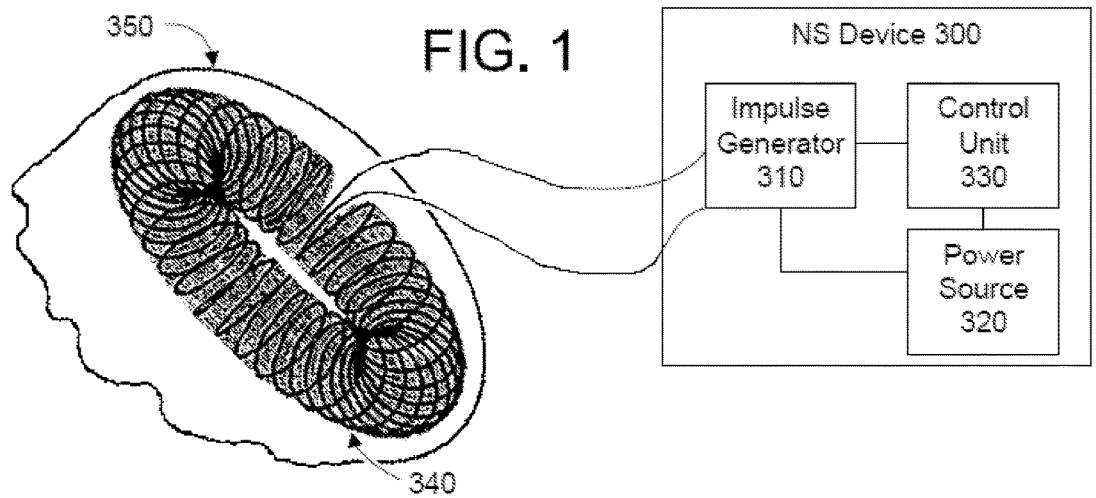
FIG. 1 is a schematic view of a nerve or tissue modulating device according to the present invention, which supplies controlled pulses of electrical current to a magnetic stimulator coil that is continuously in contact with a volume filled with electrically conducting material.

In the present invention, energy is transmitted non-invasively to a patient. In one of the preferred embodiments, a time-varying magnetic field originating outside of a patient is generated, such that the magnetic field induces an electromagnetic field and/or eddy currents within tissue of the patient. The invention is particularly useful for inducing applied electrical impulses that interact with the signals of one or more nerves, or muscles, to achieve a therapeutic result. In particular, the present disclosure describes devices and methods to treat neurodegenerative diseases, including Alzheimer's disease, Parkinson's disease, multiple sclerosis, postoperative cognitive dysfunction, and postoperative delirium.

In an exemplary embodiment, the present invention includes methods and devices for inducing, by a time-varying magnetic field, electrical fields and current within tissue, in accordance with Faraday's law of induction. Magnetic stimulation is non-invasive because the magnetic field is produced by passing a time-varying current through a coil positioned outside the body, inducing at a distance an electric field and electric current within electrically-conducting bodily tissue. Because the induced electric field and induced current depend not only upon current being passed through wire of the coil, but also upon the permeability of core material around which the coil may be wound, the term coil as used herein refers not only to the current-carrying wire, but also to the core material, unless otherwise indicated. Large, pulsed magnetic fields (PMF) can induce significant electric fields in conducting media, including human tissue. Particular waveforms and amplitudes can stimulate action potentials in nerves, both in vitro and in vivo. Due to the noninvasive nature of the stimulation, PMF devices have found utility in several clinical applications, both therapeutically, e.g., for treating depression via transcranial magnetic stimulation (TMS), and diagnostically, for peripheral nerve stimulation. It is an objective of the present invention to use magnetic stimulation to produce significantly less pain or discomfort, as compared with that experienced by the patient undergoing a treatment with TENS, for a given depth of stimulus penetration. Or conversely, for a given amount of pain or discomfort on the part of the patient (e.g., the threshold at which such discomfort or pain begins), an objective of the present invention is to achieve a greater depth of penetration of the stimulus under the skin.

The principle of operation of magnetic stimulation, along with a description of commercially available equipment and a list of medical applications of magnetic stimulation, is reviewed in: Chris HOVEY and Reza Jalinous, The Guide to Magnetic Stimulation, The Magstim Company Ltd, Spring Gardens, Whitland, Carmarthenshire, SA34 OHR, United Kingdom, 2006. The types of the magnetic stimulator coils that are described there include circular, parabolic, figure-of-eight (butterfly), and custom designs. Additional types of the magnetic stimulator coils are described in U.S. Pat. No. 6,179,770, entitled Coil assemblies for magnetic stimulators, to MOULD; as well as in Kent DAVEY. Magnetic Stimulation Coil and Circuit Design. IEEE Transactions on Biomedical Engineering, Vol. 47 (No. 11, November 2000): 1493-1499 and in HSU K H, Nagarajan S S, Durand D M. Analysis of efficiency of magnetic stimulation. IEEE Trans Biomed Eng. 2003 November; 50 (11):1276-85.

The circuits that are used to send pulses or other waveforms through magnetic stimulator coils are also described by HOVEY and Jalinous in The Guide to Magnetic Stimulation that was cited above. Custom magnetic stimulator circuits for control, impulse generator and power supply have also been described [Eric BASHAM, Zhi Yang, Natalia Tchemodanov, and Wentai Liu. Magnetic Stimulation of Neural Tissue Techniques and System Design. pp. 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to EPSTEIN; U.S. Pat. No. 5,718,662, entitled Apparatus for the magnetic stimulation of cells or tissue, to JANILOUS; U.S. Pat. No. 5,766,124, entitled Magnetic stimulator for neuro-muscular tissue, to POLSON].

As described in the above-cited publications, the circuits for magnetic stimulators are generally complex and expensive. They use a high current impulse generator that may produce discharge currents of 5,000 amps or more, which is passed through the stimulator coil, and which thereby produces a magnetic pulse. Typically, a transformer charges a capacitor in the impulse generator, which also contains circuit elements that limit the effect of undesirable electrical transients. Charging of the capacitor is under the control of a control unit, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus. Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

In the preferred embodiments of the present invention, the disclosed methods use a magnetic stimulation device that requires significantly less electrical current to be passed through its coil(s) than magnetic stimulation devices currently known in the art. That low-current magnetic stimulation device also has control circuits, impulse generators, and power supplies that are significantly less complex than magnetic stimulation devices currently known in the art. In fact, the magnetic stimulation device used in preferred embodiments of the present invention requires so little power that it can be operated using conventional low-voltage batteries, thereby reducing the cost to manufacture the device and allowing for portability of the device. The low-current magnetic stimulation device was disclosed in Applicant's co-pending U.S. patent application Ser. No. 12/964,050 entitled Magnetic Stimulation Devices and Methods of Therapy, to SIMON et al, which is hereby incorporated by reference in its entirety for all purposes.

A practical disadvantage of conventional magnetic stimulator coils is that they overheat when used over an extended period of time, because large coil currents are required to reach threshold electric fields in the stimulated tissue. At high repetition rates, currents can heat the coils to unacceptable levels in seconds to minutes, depending on the power levels and pulse durations and rates. Accordingly, coil-cooling equipment is used, which adds complexity to the magnetic stimulator coils. Two approaches to overcome heating are to cool the coils with flowing water or air or to increase the magnetic fields using ferrite cores (thus allowing smaller currents). For some applications where relatively long treatment times at high stimulation frequencies may be required, e.g. treating asthma by stimulating the vagus nerve, neither of these two approaches may be adequate. Water-cooled coils overheat in a few minutes. Ferrite core coils heat more slowly due to the lower currents and heat capacity of the ferrite core, but they also cool slowly and do not allow for water-cooling because the ferrite core occupies the volume where the cooling water would flow. One solution to this problem is to use a core that contains ferrofluids [U.S. Pat. No. 7,396,326 and published applications US20080114199, US20080177128, and US20080224808, all entitled Ferrofluid cooling and acoustical noise reduction in magnetic stimulators, respectively to GHIRON et al., RIEHL et al., RIEHL et al. and GHIRON et al.]. However, even the use of ferrofluids may be inadequate when long treatment times at high stimulation frequencies may be required.

In preferred embodiments of the present invention, applicant's above-mentioned low-current magnetic stimulation device is used, which requires so little electrical current to be passed through its coil(s) that no special cooling apparatus is required to operate the device. That device may therefore be operated at high repetition rates for an indefinite period of time. In other embodiments or the present invention, higher current magnetic stimulation coils are used, which may be cooled using methods and devices that Applicant disclosed in co-pending U.S. patent application Ser. No. 12/859,568 entitled Non-invasive Treatment of Bronchial Constriction, to SIMON, which is hereby incorporated by reference in its entirety for all purposes. That application also disclosed methods and devices for the stimulation of nerves other than magnetic stimulation devices and methods, including mechanical and/or acoustical, optical and/or thermal, and electrode-based electrical methods and devices, each of which may be used in alternate embodiments of the present invention in lieu of, or in addition to, the preferred magnetic stimulation devices and methods.

Another problem that is sometimes encountered during magnetic stimulation is the unpleasantness or pain that is experienced by the patient in the vicinity of the stimulated tissue. Little is known about the mechanism that produces the pain, although it is generally recognized that magnetic stimulation produces less pain than its electrode-based counterpart. Most investigations that address this question examine pain associated with transcranial stimulation.

ANDERSON et al found that when magnetic stimulation is repeated over the course of multiple sessions, the patients adapt to the pain and exhibit progressively less discomfort [Berry S. ANDERSON, Katie Kavanagh, Jeffrey J. Borckardt, Ziad H. Nahas, Samet Kose, Sarah H. Lisanby, William M. McDonald, David Avery, Harold A. Sackeim, and Mark S. George. Decreasing Procedural Pain Over Time of Left Prefrontal rTMS forDepression: Initial Results from the Open-Label Phase of a Multisite Trial (OPT-TMS). Brain Stimul. 2009 Apr. 1; 2(2): 88-92]. Other than waiting for the patient to adapt, strategies to reduce the pain include: use of anesthetics placed on or injected into the skin near the stimulation and placement of foam pads on the skin at the site of stimulation [Jeffrey J. BORCKARDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modelling the response of scalp sensory receptors to transcranial electrical stimulation. Med. Biol. Eng. Comput., 2002, 40, 395-401], and providing patients with the amount of information that suits their personalities [Anthony DELITTO, Michael J Strube, Arthur D Shulman, Scott D Minor. A Study of Discomfort with Electrical Stimulation. Phys. Ther. 1992; 72:410-424]. U.S. Pat. No. 7,614,996, entitled Reducing discomfort caused by electrical stimulation, to RIEHL discloses the application of a secondary stimulus to counteract what would otherwise be an uncomfortable primary stimulus.

However, these methods of reducing pain or discomfort on the part of the stimulated patient are not always successful or practical. Accordingly, in the preferred embodiments of the present invention, applicant's above-mentioned low-current magnetic stimulation device is used, which produces significantly less pain or discomfort (if any) to the patient than magnetic stimulator devices that are currently known in the art.

To achieve the objectives of the present invention, applicant's above-mentioned low-current magnetic stimulation device uses an efficient method to produce electric fields in tissue noninvasively, namely, to use a toroidal winding around a high magnetic permeability material core, embedded in a conducting medium [Rafael CARBUNARU and Dominique M. Durand. Toroidal coil models for transcutaneous magnetic stimulation of nerves. IEEE Transactions on Biomedical Engineering. 48 (No. 4, April 2001): 434-441]. The conducting medium must have direct contact with skin for current to flow from the coil into the tissue. In essence, Applicant's device produces a transcutaneous current, similar to a transcutaneous electrical nerve stimulation (TENS) device, but with greater depth of penetration and virtually no unpleasant peripheral nerve stimulation. In addition, to generate electric fields equivalent to other PMF devices, toroidal stimulators require only about 0.001-0.1 of the current and produce virtually no heating. It is understood that the magnetic field of a toroidal magnetic stimulator remains essentially within the toroid, and that when referring to this device as a magnetic stimulator, it is in fact the electric fields and/or currents that are induced outside the stimulator that produce an effect in the patient, not the magnetic field.

To the applicant's knowledge, no significant development of toroidal-coil magnetic stimulators has taken place beyond what was reported in the above-mentioned CARBUNARU and Durand publication and the dissertation upon which it was based [Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)]. Toroidal coils or partial-toroids were mentioned in the following patents or patent applications, but they did not develop the use of a conducting medium in contact with skin: US20080027513, entitled Systems And Methods For Using A Butterfly Coil To Communicate With Or Transfer Power To An Implantable Medical Device, to CARBUNARU; U.S. Pat. No. 7,361,136, entitled Method and apparatus for generating a therapeutic magnetic field, to PARKER; U.S. Pat. No. 6,527,695, entitled Magnetic stimulation coil and circuit design, to DAVEY et al.; U.S. Pat. No. 6,155,966, entitled Apparatus and method for toning tissue with a focused, coherent electromagnetic field, to PARKER; U.S. Pat. No. 4,915,110, entitled Therapeutic electrostatic device, to KITOV; US20070032827, entitled Methods and apparatus for producing therapeutic and diagnostic stimulation, to KATIMS; US20100222629, entitled Method and apparatus for magnetic induction therapy, to BURNETT et al. The latter application to BURNETT et al. only notes that "in the paper titled 'Contactless Nerve Stimulation and Signal Detection by Inductive Transducer' presented at the 1969 Symposium on Application of Magnetism in Bioengineering, Maass et al. disclosed that a nerve threading the lumen of a toroid could be stimulated by a magnetic field."

The lack of development is apparently due to the difficulty of embedding the coil in a practical conducting medium and having that medium be safely in direct contact with human skin. The only reported toroidal-coil magnetic stimulation device used to stimulate human nerves was described in the above-cited dissertation by Rafael Carbunaru FAIERSTEIN, and it embedded the coil in agar. Agar degrades in time and is not ideal to use against skin, presenting difficulties with cleaning it from a patient and within a device. Furthermore, as disclosed there, the toroid needs to be surrounded by conducting medium above, below and around it, making for a relatively bulky device that is difficult to apply to target tissue having small cross sectional area. Furthermore, the device that FAIERSTEIN discloses cannot be applied to the surface of the skin at an arbitrary orientation.

In preferred embodiments of the present invention, Applicant's low-current, toroidal-coil magnetic stimulation device is used. The device may be applied to body surfaces having an arbitrary orientation with respect to the long-axis of the component containing the coil. Additional advantages of embodiments of Applicant's device are that the embodiments are compact and portable, and that they may be adapted for use in nerve and tissue stimulation applications that treat diverse medical conditions. Applicant's co-pending patent application that was mentioned above Ser. No. 12/964,050 entitled Magnetic Stimulation Devices and Methods of Therapy, disclosed methods for using the device to treat such conditions as post-operative ileus, dysfunction associated with TNF-alpha in Alzheimer's disease, postoperative cognitive dysfunction, rheumatoid arthritis, bronchoconstriction, urinary incontinence and/or overactive bladder, and sphincter of Oddi dysfunction. The present application extends disclosure of the range of conditions that may be treated by magnetic stimulation or other non-invasive techniques, by disclosing methods and devices for treating neurodegenerative diseases more generally.

The present invention discloses methods for using vagal nerve stimulation to suppress neuroinflammation. In certain embodiments, methods and devices of the present invention involve the inhibition of pro-inflammatory cytokines, or more specifically, stimulation of the vagus nerve to inhibit and/or block the release of such pro-inflammatory cytokines. In other embodiments, the present invention discloses use of vagal nerve stimulation to increase the concentration or effectiveness of anti-inflammatory cytokines. TRACEY et al do not consider the modulation of anti-inflammatory cytokines to be part of the cholinergic anti-inflammatory pathway that their method of vagal nerve stimulation is intended to activate. Thus, they explain that "activation of vagus nerve cholinergic signaling inhibits TNF (tumor necrosis factor) and other proinflammatory cytokine overproduction through 'immune' a7 nicotinic receptor-mediated mechanisms" [V. A. PAVLOV and K. J. Tracey. Controlling inflammation: the cholinergic anti-inflammatory pathway. Biochemical Society Transactions 34, (2006, 6): 1037-1040]. In contrast, anti-inflammatory cytokines are said to be part of a different "diffusible anti-inflammatory network, which includes glucocorticoids, anti-inflammatory cytokines, and other humoral mediators" [CZURA C J, Tracey K J. Autonomic neural regulation of immunity. J Intern Med. 257(2005, 2): 156-66]. Others make a similar distinction between vagal and humoral mediation [GUYON A, Massa F, Rovère C, Nahon J L. How cytokines can influence the brain: a role for chemokines?J Neuroimmunol 2008; 198:46-55].

The disclaiming by TRACEY and colleagues of a role for anti-inflammatory cytokines as mediators of inflammation following stimulation of the vagus nerve may be due to a recognition that anti-inflammatory cytokines (e.g., TGF-β) are usually produced constitutively, while pro-inflammatory cytokines (e.g., TNF-alpha) are not produced constitutively, but are instead induced. However, anti-inflammatory cytokines are inducible as well as constitutive, so that for example, an increase in the concentrations of potentially anti-inflammatory cytokines such as transforming growth factor-beta (TGF-β) can in fact be accomplished through stimulation of the vagus nerve [R A BAUMGARTNER, V A Deramo and M A Beaven. Constitutive and inducible mechanisms for synthesis and release of cytokines in immune cell lines. The Journal of Immunology 157 (1996, 9): 4087-4093; CORCORAN, Ciaran; Connor, Thomas J; O'Keane, Veronica; Garland, Malcolm R. The effects of vagus nerve stimulation on pro- and anti-inflammatory cytokines in humans: a preliminary report. Neuroimmunomodulation 12 (5, 2005): 307-309].

An example of a pro-anti-inflammatory mechanism that is particularly relevant to the treatment of multiple sclerosis is as follows. TGF-β converts undifferentiated T cells into regulatory T (Treg) cells that block the autoimmunity that causes demyelination in multiple sclerosis. However, in the presence of interleukin-6, TGF-β also causes the differentiation of T lymphocytes into proinflammatory IL-17 cytokine-producing T helper 17 (TH17) cells, which promote autoimmunity and inflammation. Thus, it is conceivable that an increase of TGF-β levels might actually cause or exacerbate inflammation, rather than suppress it. Accordingly, a step in an embodiment of the methods that are disclosed herein is to deter TGF-β from realizing its proinflammatory potential, by selecting nerve stimulation parameters that bias the potential of TGF-β towards anti-inflammation, and/or by treating the patient with an agent such as the vitamin A metabolite retinoic acid that is known to promote such an anti-inflammatory bias [MUCIDA D, Park Y, Kim G, Turovskaya O, Scott I, Kronenberg M, Cheroutre H. Reciprocal TH17 and regulatory T cell differentiation mediated by retinoic acid. Science 317(2007, 5835): 256-60; Sheng XIAO, Hulin Jin, Thomas Korn, Sue M. Liu, Mohamed Oukka, Bing Lim, and Vijay K. Kuchroo. Retinoic acid increases Foxp3+ regulatory T cells and inhibits development of Th17 cells by enhancing TGF-β-driven Smad3 signaling and inhibiting IL-6 and IL-23 receptor expression. J Immunol. 181(2008, 4): 2277-2284]. Retinoic acid is a member of a class of compounds known as retinoids, comprising three generations: (1) retinol, retinal, retinoic acid (tretinoin, Retin-A), isotretinoin and alitretinoin; (2) etretinate and acitretin; (3) tazarotene, bexarotene and Adapalene.

In one embodiment of the invention, endogenous retinoic acid that is released by neurons themselves is used to produce the anti-inflammatory bias. Thus, it is known that vagal nerve stimulation may induce differentiation through release of retinoic acid that is produced in neurons from retinaldehyde by retinaldehyde dehydrogenases, and the disclosed invention promotes anti-inflammatory regulatory T cell (Treg) differentiation by this type of mechanism [van de PAVERT S A, Olivier B J, Goverse G, Vondenhoff M F, Greuter M, Beke P, Kusser K, Höpken U E, Lipp M, Niederreither K, Blomhoff R, Sitnik K, Agace W W, Randall T D, de Jonge W J, Mebius R E. Chemokine CXCL13 is essential for lymph node initiation and is induced by retinoic acid and neuronal stimulation. Nat Immunol. 10(11, 2009): 1193-1199].

The retinoic acid so released might also directly inhibit the release or functioning of proinflammatory cytokines, which would be an anti-pro-inflammatory mechanism that is distinct from the one proposed by TRACEY and colleagues [Malcolm Maden. Retinoic acid in the development, regeneration and maintenance of the nervous system. Nature Reviews Neuroscience 8 (2007), 755-765]. However, if the proinflammatory cytokine that is blocked is TNF-alpha, its inhibition in multiple sclerosis patients might be counterproductive. This is because blocking TNF-alpha with the drug Ienercept promotes and exacerbates multiple sclerosis attacks rather than delaying them, which might be attributable to the fact that TNF-alpha promotes remyelination and the proliferation of oligodendrocytes that perform the myelination. [ANONYMOUS. TNF neutralization in MS: Results of a randomized, placebo controlled multicenter study. Neurology 1999, 53:457; ARNETT H A, Mason J, Marino M, Suzuki K, Matsushima G K, Ting J P. TNF alpha promotes proliferation of oligodendrocyte progenitors and remyelination. Nat Neurosci 2001, 4:1116-1122].

In this example, the competence of anti-inflammatory cytokines may be modulated by the retinoic acid (RA) signaling system of the nervous system. The most important mechanism of RA activity is the regulation of gene expression. This is accomplished by its binding to nuclear retinoid receptors that are ligand-activated transcription factors. Thus, RA acts as a transcriptional activator for a large number of other, downstream regulatory molecules, including enzymes, transcription factors, cytokines, and cytokine receptors. Retinoic acid is an essential morphogen in vertebrate development and participates in tissue regeneration in the adult [Jorg M E Y and Peter MdCaffery. Retinoic Acid Signaling in the Nervous System of Adult Vertebrates. The Neuroscientist 10(5, 2004): 409-421]. RA also increases synaptic strength in a homeostatic response (synaptic scaling) to neuronal inactivity through a mechanism involving protein synthesis that requires the participation of TNF-alpha. RA is also intimately involved in the control of the rhythmic electrical activity of the brain. More generally, all-trans retinoic acid, 9-cis retinoic acid, and 13-cis retinoic acid are some of a very small number of entrainment factors that regulate the natural rhythmicity of metabolic processes in many types of individual cells [Mehdi Tafti, Norbert B. Ghyselinck. Functional Implication of the Vitamin A Signaling Pathway in the Brain. Arch Neurol. 64(12, 2007): 1706-1711].

As examples involving other neurodegenerative diseases, stimulation of nerves to enhance mechanisms involving retinoic acid or its receptors also promotes the rescue of dopamine producing cells in Parkinson's disease [Stina Friling, Maria Bergsland and Susanna Kjellander. Activation of Retinoid X Receptor increases dopamine cell survival in models for Parkinson's disease. BMC Neuroscience 2009, 10:146]. Similarly, stimulation of nerves to release retinoic acid or activate its receptors may also promote the clearance of beta amyloids in Alzheimer's disease [Camacho I. E., Serneels L., Spittaels K., Merchiers P., Dominguez D. and De Strooper B. Peroxisome-proliferator-activated receptor gamma induces a clearance mechanism for the amyloid-beta peptide. J. Neurosci. 24 (2004), 10908-10917].

The potentially anti-inflammatory cytokine TGF-beta is a member of the TGF-beta superfamily of neurotrophic factors. Neurotrophic factors serve as growth factors for the development, maintenance, repair, and survival of specific neuronal populations, acting via retrograde signaling from target neurons by paracrine and autocrine mechanisms. Other neurotrophic factors also promote the survival of neurons during neurodegeneration. These include members of the nerve growth factor (NGF) superfamily, the glial-cell-line-derived neurotrophic factor (GDNF) family, the neurokine superfamily, and non-neuronal growth factors such as the insulin-like growth factors (IGF) family. However, major problems in using such neurotrophic factors for therapy are their inability to cross the blood-brain-barrier, adverse effects resulting from binding to the receptor in other organs of the body and their low diffusion rate [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127].

It is known that vagal nerve stimulation and transcranial magnetic stimulation can increase the levels of at least one neurotrophic factor in the brain, namely, brain-derived neurotrophic factor (BDNF) in the NGF superfamily, which has been studied extensively in connection with the treatment of depression. However, vagal nerve stimulation to increase levels of neurotrophic factors has not been reported in connection with neurodegenerative diseases. Because BDNF may be modulated by stimulating the vagus nerve, vagal nerve stimulation may likewise promote the expression of other neurotrophic factors in patients with neurodegenerative disease, thereby circumventing the problem of blood-brain barrier blockage [Follesa P, Biggio F, Gorini G, Caria S, Talani G, Dazzi L, Puligheddu M, Marrosu F, Biggio G. Vagus nerve stimulation increases norepinephrine concentration and the gene expression of BDNF and bFGF in the rat brain. Brain Research 1179 (2007): 28-34; Biggio F, Gorini G, Utzeri C, Olla P, Marrosu F, Mocchetti I, Follesa P. Chronic vagus nerve stimulation induces neuronal plasticity in the rat hippocampus. Int J. Neuropsychopharmacol. 12(9, 2009):1209-21; Roberta Zanardini, Anna Gazzoli, Mariacarla Ventriglia, Jorge Perez, Stefano Bignotti, Paolo Maria Rossini, Massimo Gennarelli, Luisella Bocchio-Chiavetto. Effect of repetitive transcranial magnetic stimulation on serum brain derived neurotrophic factor in drug resistant depressed patients. Journal of Affective Disorders 91 (2006) 83-86]. Patent application US20100280562, entitled Biomarkers for monitoring treatment of neuropsychiatric diseases, to PI et al, disclosed the measurement of GDNF and other neurotrophic factors following vagal nerve stimulation. However, that application is concerned with the search for biomarkers involving the levels of GDNF, rather than a method for treating a neurodegenerative disease using vagal nerve stimulation.

FIG. 1 is a schematic diagram of a nerve stimulating/modulating device 300 for delivering impulses of energy to nerves for the treatment of medical conditions. As shown, device 300 may include an impulse generator 310; a power source 320 coupled to the impulse generator 310; a control unit 330 in communication with the impulse generator 310 and coupled to the power source 320; and a magnetic stimulator coil 340 coupled via wires to impulse generator coil 310. The stimulator coil 340 is toroidal in shape, due to its winding around a toroid of core material.

Although the magnetic stimulator coil 340 is shown in FIG. 1 to be a single coil, in practice the coil may also comprise two or more distinct coils, each of which is connected in series or in parallel to the impulse generator 310. Thus, the coil 340 shown in FIG. 1 represents all the magnetic stimulator coils of the device collectively. In the preferred embodiment that is disclosed below, coil 340 actually contains two coils that may be connected either in series or in parallel to the impulse generator 310.

The item labeled in FIG. 1 as 350 is a volume, surrounding the coil 340, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 350 correspond also to sinuousness or curvature on the surface of the body, against which the conducting medium 350 is applied, so as to make the medium and body surface contiguous. As described below in connection with a preferred embodiment, the volume 350 is electrically connected to the patient at a target skin surface in order to significantly reduce the current passed through the coil 340 that is needed to accomplish stimulation of the patient's nerve or tissue. As also described below in connection with a preferred embodiment, conducting medium in which the coil 340 is embedded need not completely surround the toroid.

The control unit 330 controls the impulse generator 310 to generate a signal for each of the device's magnetic stimulation coils. The signals are selected to be suitable for amelioration of a particular medical condition, when the signals are applied non-invasively to a target nerve or tissue via the magnetic stimulator coil 340. It is noted that nerve stimulating/modulating device 300 may be referred to by its function as a pulse generator. Patent application publications US2005/0075701 and US2005/0075702, both to SHAFER, both of which are incorporated herein by reference, relating to stimulation of neurons of the sympathetic nervous system to attenuate an immune response, contain descriptions of pulse generators that may be applicable to the present invention, when adapted for use with a magnetic stimulator coil. By way of example, a pulse generator 300 is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals.

Parameters for the nerve or tissue stimulation include power level, frequency and train duration (or pulse number). The stimulation characteristics of each pulse, such as depth of penetration, strength and accuracy, depend on the rise time, peak electrical energy transferred to the coil and the spatial distribution of the electric field. The rise time and peak coil energy are governed by the electrical characteristics of the magnetic stimulator and stimulating coil, whereas the spatial distribution of the induced electric field depends on the coil geometry and the anatomy of the region of induced current flow. In one embodiment of the invention, pulse parameters are set in such as way as to account for the detailed anatomy surrounding the nerve that is being stimulated [Bartosz SAWICKI, Robert Szmurto, Przemystaw Ptonecki, Jacek Starzyński, Stanistaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. A single pulse may be monophasic (no current reversal within the coil), biphasic or polyphasic. For rapid rate stimulators, biphasic systems may be used wherein energy is recovered from each pulse in order to help energize the next. Embodiments of the invention include those that are fixed frequency, where each pulse in a train has the same inter-stimulus interval, and those that have modulated frequency, where the intervals between each pulse in a train can be varied.

Figure 2:
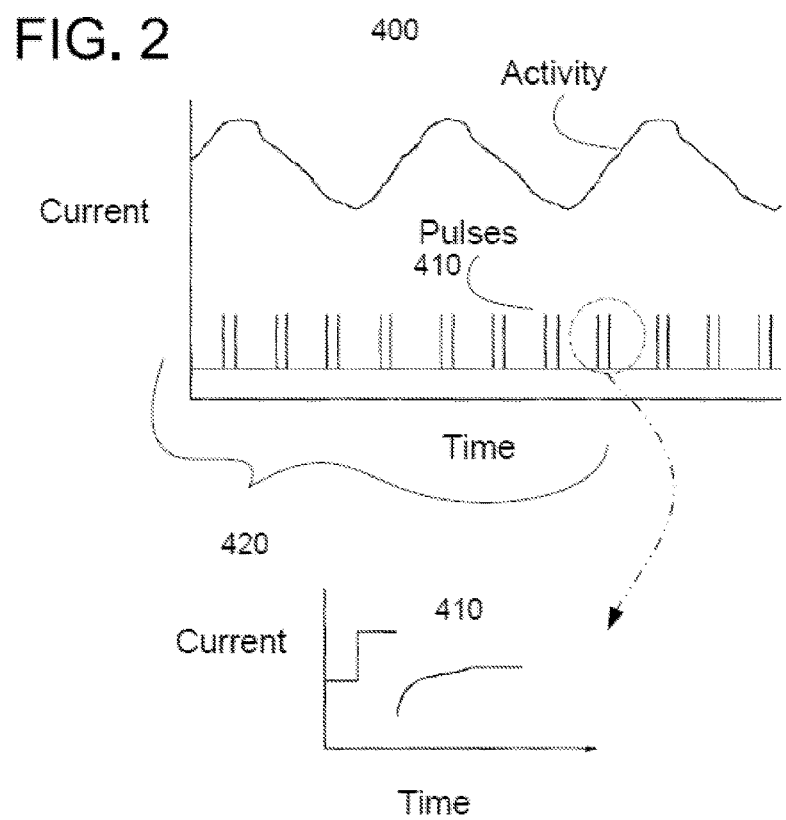
FIG. 2 illustrates an exemplary electrical voltage/current profile for a blocking and/or modulating impulses that are applied to a portion or portions of a nerve, in accordance with an embodiment of the present disclosure.

FIG. 2 illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively induced within the patient by the magnetic stimulator. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the stimulator coils(s) 340 that deliver the stimulating, blocking and/or modulating impulse 410 to the nerve. Nerve stimulating/modulating device 300 may be externally powered and/or recharged may have its own power source 320.

The parameters of the modulation signal 400 are preferably programmable, such as the frequency, amplitude, duty cycle, pulse width, pulse shape, etc. An external communication device may modify the pulse generator programming to improve treatment.

In addition, or as an alternative to the devices to implement the modulation unit for producing the electrical voltage/current profile of the stimulating, blocking and/or modulating impulse to the magnetic stimulator coil, the device disclosed in patent publication No. US2005/0216062 (the entire disclosure of which is incorporated herein by reference) may be employed. U.S. Patent Publication No.: 2005/0216062 discloses a multifunctional electrical stimulation (ES) system adapted to yield output signals for effecting electromagnetic or other forms of electrical stimulation for a broad spectrum of different biological and biomedical applications, including magnetic stimulators, which produce a high intensity magnetic field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

The preferred embodiment of magnetic stimulator coil 340 comprises a toroidal winding around a core consisting of high-permeability material (e.g., Supermendur), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface. [Rafael CARBUNARU and Dominique M. Durand. Toroidal coil models for transcutaneous magnetic stimulation of nerves. IEEE Transactions on Biomedical Engineering 48 (No. 4, April 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.)].

In order to explain some of the novelty of the presently disclosed invention as compared with the device described in the above-mentioned Carbunaru and Durand publication, as well as in the FAIERSTEIN dissertation upon which the publication was based, it is useful to first summarize the relevant physics of electric fields and currents that are induced by time-varying magnetic fields, as produced by current-carrying coils [Richard P. FEYNMAN, Robert B. Leighton, and Matthew Sands. The Feynman Lectures on Physics. Volume II. Addison-Wesley Publ. Co. (Reading M A, 1964), page 15-15; K. P. ESSELLE and M. A. Stuchly, Neural stimulation with magnetic fields: Analysis of induced electric fields, IEEE Trans. Biomed. Eng., 39 (July 1992), pp. 693-700; R. BOWTELL and R. M. Bowley. Analytic Calculations of the E-Fields Induced by Time-Varying Magnetic Fields Generated by Cylindrical Gradient Coils. Magnetic Resonance in Medicine 44:782-790 (2000); Feng LIU, Huawei Zhao, and Stuart Crozier. On the Induced Electric Field Gradients in the Human Body for Magnetic Stimulation by Gradient Coils in MRI, IEEE Transactions on Biomedical Engineering 50: (No. 7, July 2003) pp. 804-815].

The magnetic field B may be represented as the curl of a vector potential A, where B and A are functions of position and time: B=∇×A.

The electric field E, which is also a function of position and time, consists of two parts, $E_1$ and $E_2$: $E=E_1+E_2$. For a current-carrying coil, $E_1$ is obtained from the vector potential A by:

$$E_1 = -\frac{\partial A}{\partial t} = -\int \frac{1}{4\pi} \frac{\partial(\mu I)}{\partial t} \frac{dl}{r}$$

where $\mu$ is the permeability, I is the current flowing in the coil, dl is an oriented differential element of the coil, r is the distance between dl and the point at which the electric field E is measured, and the integral is performed around all the differential elements dl of the coil.

$E_2$ is obtained from the gradient of a scalar potential $\Phi$: $E_2 = -\nabla\Phi$. The scalar potential arises because conductivity changes along the path of a current, particularly the abrupt change of conductivity at an air/conductor interface, causes electric charges to separate and accumulate on the surface of the interface, with the amplitude and sign of the charges changing as a function of surface position. Thus, no conduction current can flow across an air/conductor interface, so according to the interfacial boundary conditions, the component of any induced current normal to the interface must be zero. The existence of a scalar potential accounts for these effects.

The electrical current density J, which is also a function of position and time, consists of two parts: $J=J_1+J_2$, corresponding to the two parts of E: $J_1=\sigma E_1$ and $J_2=\sigma E_2$, where the conductivity $\sigma$ is generally a tensor and a function of position. If the current flows in material that is essentially unpolarizable (i.e., is presumed not to be a dielectric), any displacement current may be ignored, so the current would satisfy Ampere's law:

$$\nabla \times \frac{B}{\mu} = J.$$

Because the divergence of the curl is zero, $\nabla \cdot J=0$. One may substitute $J_1$ and $J_2$ into that equation to obtain: $\nabla\cdot(\sigma[((E)]_1 1-\nabla\Phi))=0$. The latter equation has been solved numerically for special cases to estimate the currents that are induced by a magnetic field that is inserted into the body [W. WANG, S. R. Eisenberg, A three-dimensional finite element method for computing magnetically induced currents in tissues. IEEE Transactions on Magnetics. 30 (6, November 1994): 5015-5023; Bartosz SAWICKI, Robert Szmurto, Przemystaw Ptonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. If the conductivity of material in the device (or patient) is itself selected to be a function of the electric field, then the equation becomes non-linear, which could exhibit multiple solutions, frequency multiplication, and other such non-linear behavior.

If the displacement current cannot be ignored, the displacement appears as a term involving the time-derivative of the electric field in the more general expression:

$$\nabla \cdot \left( \frac{\partial(\epsilon E)}{\partial t} + \cdot\sigma[((E)]_1 1 - \nabla\Phi) \right) = 0$$

where ∈ is the permittivity, which is a function of position and is generally a tensor. As a consequence of such a term, the waveform of the electric field at any point will generally be altered relative to the waveform of the current I(t) that is passed through the coils. Furthermore, if the permittivity of a material in the device is itself selected to be a function of the electric field, then the equation becomes non-linear, which could exhibit multiple solutions, frequency multiplication, and other such non-linear behavior.

The above-mentioned publication by CARBUNARU and Durand, as well as the FAIERSTEIN dissertation upon which the publication was based, are heretofore unique in that they describe a magnetic stimulation device that does not create a magnetic field within the tissues that the device is intended to stimulate. Their device instead confines the magnetic field to a toroid, which is the only coil geometry known to create a magnetic field that is completely limited to part of space. With such a device, the electric field alone penetrates the patient to stimulate nerves or tissue, which they calculate using device-specific equations for the fields $E_1$ and $E_2$ that were defined above. Unlike conventional magnetic stimulation devices, their device's electric field orientation is not limited to fields at the skin that are parallel to the skin surface, due to the presence of conducting material that extends from the skin to (and beyond) the stimulator's coil. The boundary conditions giving rise to $E_2$ were those of an infinite half-space. Thus, their toroidal coil was immersed in a homogeneous continuous conducting material that had an air/conductor interface along an infinite plane parallel to the toroid, located at a variable distance from the toroid, and the toroid and conducting material were in contact with a patient's skin.

In their investigations, Carbunaru and Durand varied $E_1$ by only changing the coil geometry (integral over dl) as follows. They investigated winding the coil around different core geometries (round, quarter circle, square) and changed the radius and thickness of the core. They also varied $E_2$ by varying the thickness of the conducting layer in which the toroid was immersed, thereby changing boundary conditions only in that manner. Although Carbunaru and Durand demonstrated that it is possible to electrically stimulate a patient transcutaneously with such a device, they made no attempt to develop the device in such a way as to generally shape the electric field that is to stimulate the nerve. In particular, the electric fields that may be produced by their device are limited to those that are radially symmetric at any given depth of stimulation into the patient (i.e., z and p are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein. Accordingly, it is an objective of the present invention to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions.

Thus, the present invention differs from the device disclosed by CARBUNARU and Durand by deliberately shaping an electric field that is used to transcutaneously stimulate the patient. Our invention does so by configuring elements that are present within the equations that were summarized above, comprising (but not limited to) the following exemplary configurations that may be used alone or in combination.

First, the contours of the coil differential elements dl that are integrated in the above equation for $E_1$ are shaped into a geometry other than a single planar toroid. For example, two separate toroidal coils are used so that $E_1$ becomes the sum of two integrals, or the shape of a single toroid is twisted to resemble a figure-of-8 rather than a planar toroid.

Second, the value of the current I in the above equation for $E_1$ is manipulated to shape the electric field. For example, if the device contains two toroidal coils, the current in one toroid may be the negative of the current in the other toroid. As another example, the magnitude of the current in a left toroidal coil may be varied relative to the magnitude of the current in a right toroidal coil, so that the location of their superimposed induced electric fields may be correspondingly moved (focused) in the left or right directions. As another example, the waveform of the current in a left toroidal coil may be different than the waveform of the current in a right toroidal coil, so that their superimposed induced electric fields may exhibit beat frequencies, as has been attempted with electrode-based stimulators [U.S. Pat. No. 5,512,057, entitled Interferential stimulator for applying localized stimulation, to REISS et al.], and acoustic stimulators [Patent No. U.S. Pat. No. 5,903,516, entitled Acoustic force generator for detection, imaging and information transmission using the beat signal of multiple intersecting sonic beams, to GREENLEAF et al].

Third, the scalar potential Φ in the above equation for $E_2$ is manipulated to shape the electric field. For example, this is accomplished by changing the boundaries of conductor/air (or non-conductor) interfaces, thereby creating different boundary conditions. Whereas the toroid in the CARBUNARU and Durand publication was immersed in a homogeneous conducting half-space, this is not necessarily the case for our invention. Although our invention will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima.

Fourth, the conductivity σ (in the equations $J_1=\sigma E_1$ and $J_2=\sigma E_2$) may be varied spatially within the device by using two or more different conducting materials that are in contact with one another, for given boundary conditions. The conductivity may also be varied by constructing some conducting material from a semiconductor, which allows for adjustment of the conductivity in space and in time by exposure of the semiconductor to agents to which they are sensitive, such as electric fields, light at particular wavelengths, temperature, or some other environmental variable over which the user of the device has control. For the special case in which the semiconductor's conductivity may be made to approach zero, that would approximate the imposition of an interfacial boundary condition as described in the previous paragraph. As another example, the conducting material of the device may be selected to have a three-dimensional conductivity structure that approximates that of the conducting tissue under the patient's skin, but oriented in the opposite and/or mirror image directions, in such a way that the conductivity is symmetrical on either side of the patient's skin. Such an arrangement will allow for essentially symmetrical electrical stimulation of the patient's tissue and the conducting material within the device.

Fifth, a dielectric material having a high permittivity ∈, such as Mylar, neoprene, titanium dioxide, or strontium titanate, may be used in the device, for example, in order to permit capacitative electrical coupling to the patient's skin.

Sixth, the present invention is more general than the device described in the above-mentioned publication of CARBUNARU and Durand in that, although the magnetic field produced by the present invention does not effectively penetrate the patient's tissue, that feature need not be due to the use of a toroidal coil. The magnetic field will not effectively penetrate the patient's tissue if the field's de minimis existence within the patient would produce no significant physiological effect. For example, it would not produce a significant physiological effect if the magnitude of the magnetic field were of the same order of magnitude as the earth's magnetic field. The magnetic field of our disclosed device may be produced by a coil other than a toroid, wherein the magnetic field outside the coil falls rapidly as a function of distance from the coil. For example, the coil may be a solenoid that has an approximately centrally-confined magnetic field as the density of coil turns and the length of the solenoid increase. As another example, the coil may be a partial toroid, which would also have a magnetic field that approximates that of a complete toroid as the gap within the partial-toroid decreases to zero. As another example, even if one is attempting to construct a complete toroidal winding, the presence of lead wires and imperfections of the winding may cause the device in practice to deviate from the ideal toroid. Such non-toroidal windings may be used in the present invention if they are backed away and/or oriented relative to the patient's skin in such a way that the magnetic field that is produced by the device does not effectively penetrate the patient's tissue. Alternatively, magnetic shielding, such as mumetal, supermalloy, supermumetal, nilomag, sanbold, molybdenum permalloy, Sendust, M-1040, Hipernom and HyMu-80, may be interposed between the patient and coil of the device in such a way that the magnetic field that is produced by the device does not effectively penetrate the patient's tissue.

In the dissertation cited above, Carbunaru-FAIERSTEIN made no attempt to use conducting material other than agar in a KCl solution, and he made no attempt to devise a device that could be conveniently and safely applied to a patient's skin, at an arbitrary angle without the conducting material spilling out of its container. It is therefore an objective of the present invention to disclose conducting material that can be used not only to adapt the conductivity σ and select boundary conditions, thereby shaping the electric fields and currents as described above, but also to create devices that can be applied practically to any surface of the body. The volume of the container containing electrically conducting medium is labeled in FIG. 1 as 350. Use of the container of conducting medium 350 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. This allows for minimal heating and deeper tissue stimulation. However, application of the conducting medium to the surface of the patient is difficult to perform in practice because the tissue contours (head for TMS, arms, legs, neck, etc. for peripheral nerve stimulation) are not planar. To solve this problem, in the preferred embodiment of the present invention, the toroidal coil is embedded in a structure which is filled with a conducting medium having approximately the same conductivity as muscle tissue, as now described.

In one embodiment of the invention, the container contains holes so that the conducting material (e.g., a conducting gel) can make physical contact with the patient's skin through the holes. For example, the conducting medium 350 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present invention is able to stimulate body surfaces having arbitrary orientation. Examples making use of the present device show the body surface as having many different orientations that are incompatible with the disclosure in the above-cited dissertation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 1-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J. Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNAGEL Electrode Gel from Parker Laboratories, Inc., 286 Eldridge Rd., Fairfield N.J. 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 340 in FIG. 1 reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

This preferred embodiment of the invention is shown in FIG. 3. FIGS. 3A and 3B respectively provide top and bottom views of the outer surface of the toroidal magnetic stimulator 30. FIGS. 3C and 3D respectively provide top and bottom views of the toroidal magnetic stimulator 30, after sectioning along its long axis to reveal the inside of the stimulator.

FIGS. 3A-3D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

Figure 3A:
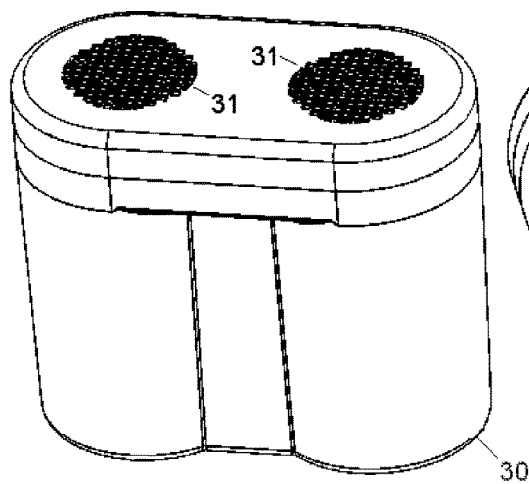
FIGS. 3A and 3B illustrate top and bottom views respectively of a toroidal magnetic stimulator in an embodiment of the present invention.
Figure 3B:
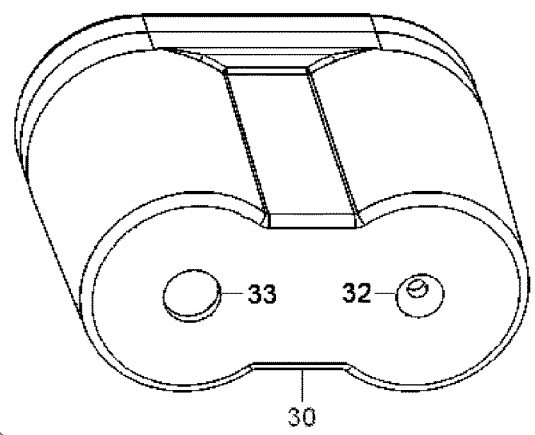
Figure 3C:
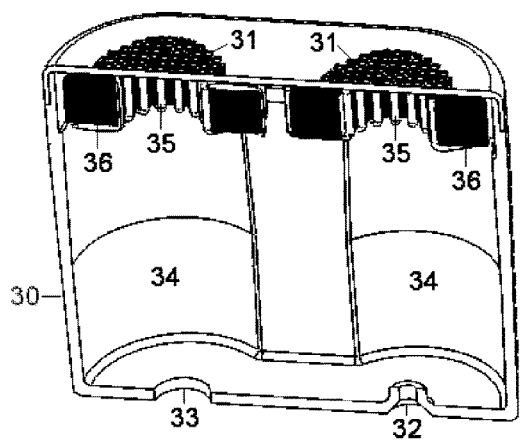
FIGS. 3C and 3D illustrate top and bottom views respectively of a toroidal magnetic stimulator of an embodiment after sectioning along its long axis to reveal the inside of the stimulator in an embodiment.
Figure 3D:
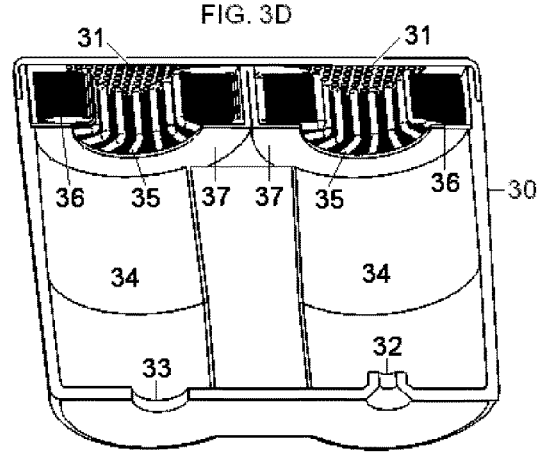

FIGS. 3B-3D show openings at the opposite end of the stimulator 30. One of the openings is an electronics port 32 through which wires pass from the stimulator coil(s) to the impulse generator (310 in FIG. 1). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 3C and 3D. The depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (No. 4, April 2001): 434-441].

FIGS. 3C and 3D also show the coils of wire 35 that are wound around toroidal cores 36, consisting of high-permeability material (e.g., Supermendur). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 3C and 3D, the coils 35 and cores 36 around which they are wound are mounted as close as practical to the corresponding mesh 31 with openings through which conducting gel passes to the surface of the patient's skin. As seen in FIG. 3D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

The embodiment shown in FIG. 3 contains two toroids, in which the outer surface of the toroids are planar, the toroids lie side-by-side, and the corresponding outer surfaces for both toroids lie essentially in the same plane. Many different embodiments are also contemplated, each of which may be better suited to the stimulation of particular nerves or tissues. Examples of such alternate embodiments are illustrated in FIG. 4, showing the geometry of the toroidal core material around which coils of wire (not shown) would be wound. The darkened faces of the figures shown there indicate the faces that would be oriented towards the patient's skin. Instead of placing the toroids side-by-side as in FIG. 3, a pair of toroids may be placed concentrically as shown in FIG. 4A. Instead of using two toroids, any number could be used, as illustrated by FIG. 4B that shows four concentrically positioned toroids. Individual planar toroids need not all lie in the same plane, as shown in FIG. 4C. In fact, the toroids themselves need not have a planar structure, as illustrated in FIGS. 4D and 4E. Furthermore, the toroids need not have a round structure or a structure comprising arcs, as illustrated in FIG. 4F, which shows a pair of concentrically positioned square toroids. The examples shown here have toroids that are rectangular or square when sectioned perpendicular to their perimeters. In other embodiments, the sectioned toroid could have any other closed geometry, such as a circle or an ellipse or a geometry that changes from one part of the toroid to another.

Thus, the geometrical configuration of the disclosed device is general. For example, it may comprise a plurality of toroids. It may comprise two toroids wherein one toroid lies within the aperture of the second toroid. A surface having a minimum area that fills an aperture of a toroid need not lie within a plane. The projection of the volume of a toroidal core onto a plane need not produce a circular shape around any perimeter of any such projection. For a plurality of toroids, a plane having a greatest area of intersection through one toroid among the plurality may, but need not, be parallel to a plane having a greatest area of intersection through some second toroid among the plurality.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff Mt A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology. vol 85, pp. 253-264, 1992; Nafia AL-MUTAWALY, Hubert de Bruin, and Gary Hasey. The Effects of Pulse Configuration on Magnetic Stimulation. Journal of Clinical Neurophysiology 20(5):361-370, 2003].

In the preferred embodiment of the invention, electronic components of the stimulator (impulse generator, control unit, and power source) are compact, portable, and simple to operate. The preferred simplicity is illustrated in FIG. 5, which shows the stimulator coil housing 30 (illustrated in more detail as 30 in FIG. 3), which is connected by electrical cable to a circuit control box 38. As shown in FIG. 5, the circuit control box 38 will generally require only an on/off switch and a power controller, provided that the parameters of stimulation described in connection with FIG. 2 have already been programmed for the particular application of the device. For such a portable device, power is provided by batteries, e.g., a 9 volt battery or two to six 1.5V AA batteries. A covering cap 39 is also provided to fit snugly over the mesh (31 in FIG. 3) of the stimulator coil housing 30, in order to keep the housing's conducting medium from leaking or drying when the device is not in use.

In the preferred embodiment for a generic therapeutic application, the currents passing through the coils of the magnetic stimulator will saturate the core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses. The burst repeats at 1 Hz to 5000 Hz, preferably at 15-50 Hz. The pulses have duration of 20 to 1000 microseconds, preferably 200 microseconds and there may be 1 to 20 pulses per burst. Other waveforms described above in connection with FIG. 2 are also generated, depending on the nerve or tissue stimulation application.

Examples in the remaining disclosure will be directed to use of the disclosed toroidal magnetic stimulation device for treatment of specific medical conditions. These applications involve stimulating a patient in and around the patient's neck. However, it will be appreciated that the systems and methods of the present invention can be applied equally well to other tissues and nerves of the body, including but not limited to parasympathetic nerves, sympathetic nerves, spinal or cranial nerves, and brain tissue. In addition, the present invention can be used to directly or indirectly stimulate or otherwise modulate nerves that innervate smooth or skeletal muscle, endocrine glands, and organs of the digestive system.

In some preferred embodiments of methods that make use of the disclosed toroidal-coil magnetic stimulation device, selected nerve fibers are stimulated. These include stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is ordinarily selected for stimulation because stimulation of the right vagus nerve may produce undesired effects on the heart.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
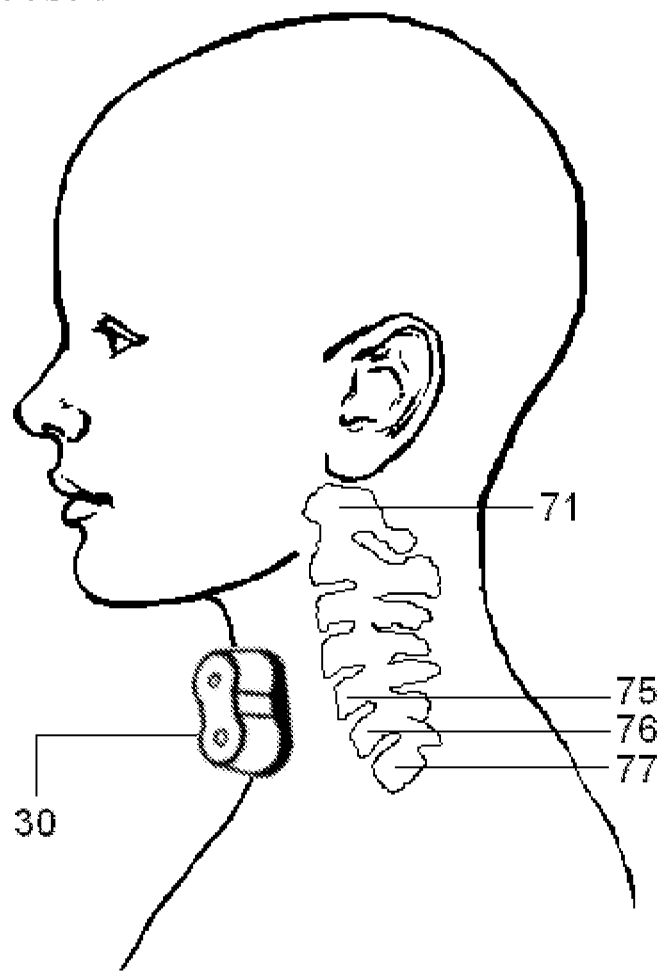
FIG. 6 illustrates the approximate position of the housing of the magnetic stimulator coil according one embodiment of the present disclosure, when the coil is used to stimulate the vagus nerve in the neck of a patient.

FIG. 6 illustrates use of the device shown in FIG. 3 and FIG. 5 to stimulate the vagus nerve at that location in the neck, in which the stimulator device 30 is applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 7:
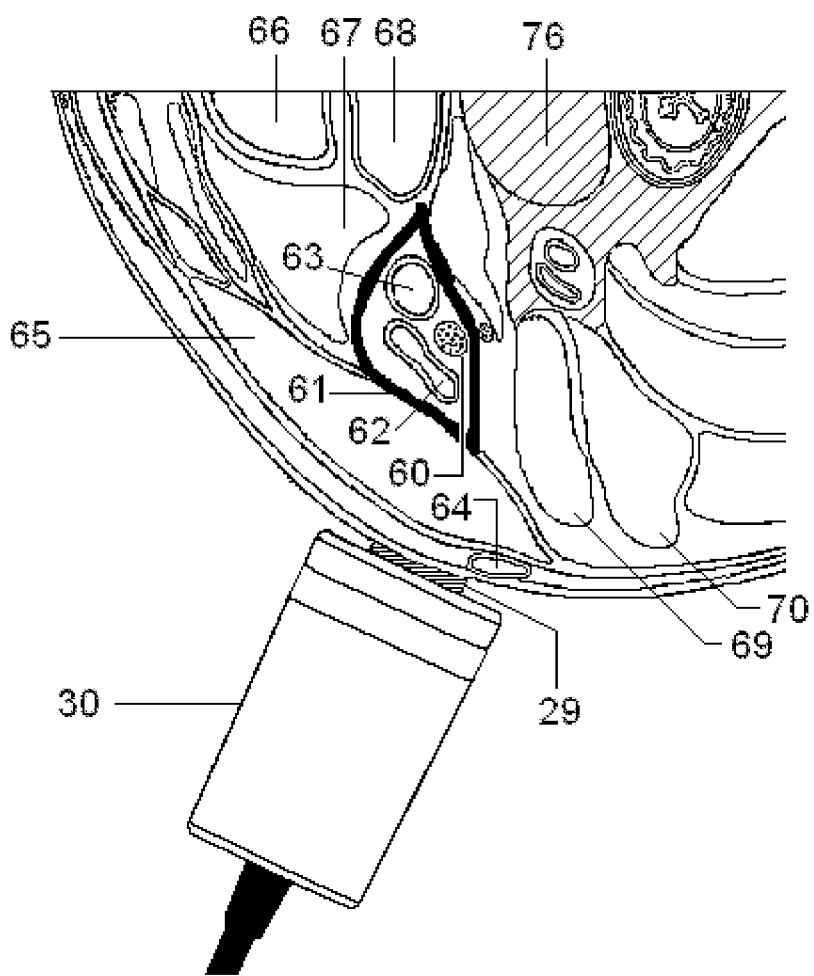
FIG. 7 illustrates the housing of the magnetic stimulator coil according one embodiment of the present invention, as the coil is positioned to stimulate the vagus nerve in a patient's neck via electrically conducting gel (or some other conducting material), which is applied to the surface of the neck in the vicinity of the identified anatomical structures.

FIG. 7 provides a more detailed view of use of the toroidal magnetic stimulator device, when positioned to stimulate the vagus nerve at the neck location that is indicated in FIG. 6. As shown, the toroidal magnetic stimulator 30 touches the neck indirectly, by making electrical contact through conducting gel 29 (or other conducting material) that is dispensed through mesh openings of the stimulator (identified as 31 in FIG. 3). The layer of conducting gel 29 in FIG. 7 is shown to connect the device to the patient's skin, but it is understood that the actual location of the gel layer(s) is generally determined by the location of mesh 31 shown in FIG. 3A. It is also understood that the device 30 is connected via wires or cables (not shown) to an impulse generator 310 as in FIG. 1. The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Magnetic stimulation has been used by several investigators to non-invasively stimulate the vagus nerve, in the neck and at other locations. In a series of articles beginning in 1992, Aziz and colleagues describe using non-invasive magnetic stimulation to electrically stimulate the vagus nerve in the neck. [Q. AZIZ et al. Magnetic Stimulation of Efferent Neural Pathways to the Human Oesophagus. Gut 33: S53-S70 (Poster Session F218) (1992); AZIZ, Q., J. C. Rothwell, J. Barlow, A. Hobson, S. Alani, J. Bancewicz, and D. G. Thompson. Esophageal myoelectric responses to magnetic stimulation of the human cortex and the extracranial vagus nerve. Am. J. Physiol. 267 (Gastrointest. Liver Physiol. 30): G827-G835, 1994; Shaheen HAMDY, Qasim Aziz, John C. Rothwell, Anthony Hobson, Josephine Barlow, and David G. Thompson. Cranial nerve modulation of human cortical swallowing motor pathways. Am. J. Physiol. 272 (Gastrointest. Liver Physiol. 35): G802-G808, 1997; Shaheen HAMDY, John C. Rothwell, Qasim Aziz, Krishna D. Singh, and David G. Thompson. Long-term reorganization of human motor cortex driven by short-term sensory stimulation. Nature Neuroscience 1 (issue 1, May 1998):64-68.] SIMS and colleagues stimulated the vagus nerve at and near the mastoid tip. [H. Steven SIMS, Toshiyuki Yamashita, Karen Rhew, and Christy L. Ludlow. Assessing the clinical utility of the magnetic stimulator for measuring response latencies in the laryngeal muscles. Otolaryngol Head Neck Surg 1996; 114:761-7]. KHEDR and colleagues also used a magnetic stimulator to stimulate the vagus nerve at the tip of the mastoid bone [E. M. KHEDR and E-E. M. Aref Electrophysiological study of vocal-fold mobility disorders using a magnetic stimulator. European Journal of Neurology 2002, 9: 259-267; KHEDR, E. M., Abo-Elfetoh, N., Ahmed, M. A., Kamel, N. F., Farook, M., El Karn, M. F. Dysphagia and hemispheric stroke: A transcranial magnetic study. Neurophysiologie Clinique/Clinical Neurophysiology (2008) 38, 235-242)]. SHAFIK stimulated the vagus nerve in the neck, placing the magnetic stimulator on the neck between the sternomastoid muscle and the trachea. [A. SHAFIK. Functional magnetic stimulation of the vagus nerve enhances colonic transit time in healthy volunteers. Tech Coloproctol (1999) 3:123-12]. Among these investigations, the one by SHAFIK stimulated the vagus nerve for the longest period of time. He stimulated at 175 joules per pulse, 40 Hz frequency, 10 seconds on, 10 seconds off for 20 minutes duration and followed by 60 minutes of rest, and this sequence was performed for 5 cycles in each subject.

The vagus is not the only nerve that may be stimulated non-invasively in the neck using magnetic stimulation. For example, the phrenic nerve has also been magnetically stimulated. [SIMILOWSKI, T., B. Fleury, S. Launois, H. P. Cathala, P. Bouche, and J. P. Derenne. Cervical magnetic stimulation: a new painless method for bilateral phrenic nerve stimulation in conscious humans. J. Appl. Physiol. 67(4): 1311-1318, 1989; Gerrard F. RAFFERTY, Anne Greenough, Terezia Manczur, Michael I. Polkey, M. Lou Harris, Nigel D. Heaton, Mohamed Rela, and John Moxham. Magnetic phrenic nerve stimulation to assess diaphragm function in children following liver transplantation. Pediatr Crit Care Med 2001, 2:122-126; W. D-C. MAN, J. Moxham, and M. I. Polkey. Magnetic stimulation for the measurement of respiratory and skeletal muscle function. Eur Respir J 2004; 24: 846-860]. If one intends to stimulate only the vagus nerve, careful positioning of the stimulator coil should be undertaken in order to avoid co-stimulation of the phrenic nerve, or the magnetic stimulation waveform may be designed to minimize the effect of any co-stimulation of the vagus and phrenic nerves [patent application JP2008/081479A, entitled Vagus nerve stimulation system, to YOSHIHOTO].

If it is desired to maintain a constant intensity of stimulation in the vicinity of the vagus nerve (or any other nerve or tissue that is being stimulated), methods may also be employed to modulate the power of the stimulator in order to compensate for patient motion or other mechanisms that would otherwise give rise to variability in the intensity of stimulation. In the case of stimulation of the vagus nerve, such variability may be attributable to the patient's breathing, which may involve contraction and associated change in geometry of the sternocleidomastoid muscle that is situated close to the vagus nerve (identified as 65 in FIG. 7). Methods for compensating for motion and other confounding factors were disclosed by the present applicant in co-pending application Ser. No. 12/859,568 entitled Non-Invasive Treatment of Bronchial Constriction, to SIMON, which is hereby incorporated by reference.

Several examples follow, exemplifying therapies for neurodegenerative disorders that involve stimulation of the vagus nerve in the neck using magnetic stimulation devices. However, it is understood that stimulation of the vagus nerve could also be performed at locations other than the neck [Polak T, Markulin F, Ehlis A C, Langer J B, Ringel T M, Fallgatter A J. Far field potentials from brain stem after transcutaneous vagus nerve stimulation: optimization of stimulation and recording parameters. J Neural Transm. 2009 October; 116(10):1237-42]. It is also understood that non-invasive methods other than magnetic stimulation may also be used to stimulate the vagus nerve, in order to achieve the intended therapeutic effects. In particular, the non-invasive methods and devices that Applicant disclosed in co-pending U.S. patent application Ser. No. 12/859,568 entitled Non-invasive Treatment of Bronchial Constriction, to SIMON, may also be used. It is also understood that stimulation of nerves other than the vagus nerve may also achieve the intended therapeutic results, including those in the sympathetic nervous system, particularly the splenic nerve.

Figure 8:
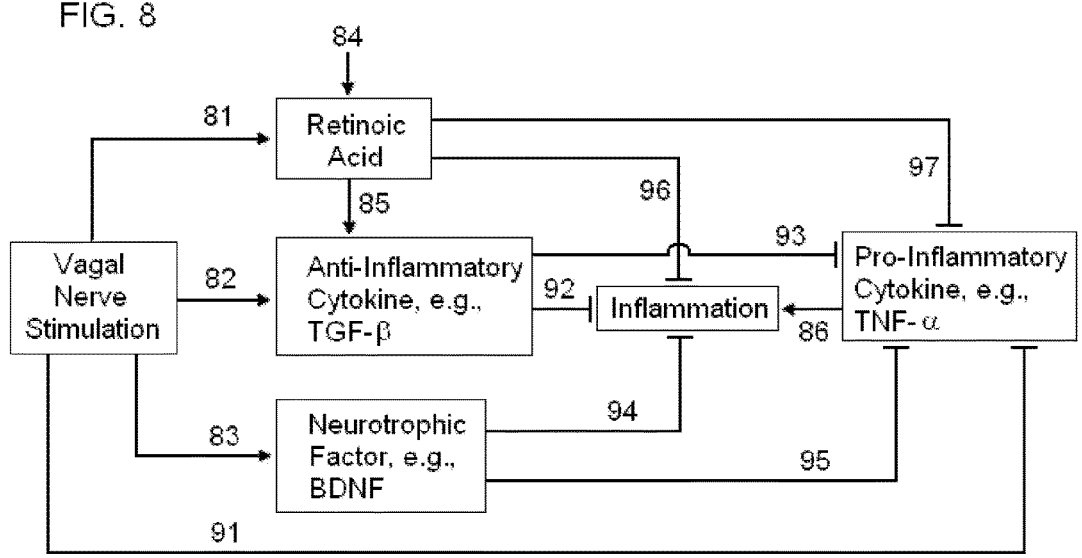
FIG. 8 illustrates mechanisms or pathways through which stimulation of the vagus nerve may reduce inflammation in patients with neurodegenerative disorders.

FIG. 8 illustrates mechanisms or pathways through which stimulation of the vagus nerve may be used to reduce inflammation in patients with neurodegenerative disorders. In what follows, each of the mechanisms or pathways is described in connection with treatment of particular disorders, namely, Alzheimer's disease, Parkinson's disease, multiple sclerosis, and postoperative cognitive dysfunction and/or postoperative delirium. However, it is understood that the treatment of other neurodegenerative disorders using vagal nerve stimulation may also make use of methods involving these mechanisms or pathways. It is also understood that not all of the pathways or mechanisms may be used in the treatment of a particular patient and that pathways or mechanisms that are not shown in FIG. 8 may also be used. Thus, particular pathways or mechanisms are invoked by the selection of particular stimulation parameters, such as current, frequency, pulse width, duty cycle, etc. Nevertheless, as an aid to understanding the applications that follow, it is useful to consider at once all the mechanisms shown in FIG. 8.

Two types of pathways are shown in FIG. 8. The pathways that stimulate or upregulate are indicated with an arrow (↓). The pathways that inhibit or downregulate are indicated with a blockage bar (⊥). Pathways resulting from stimulation of the vagus nerve are shown to stimulate retinoic acid 81, anti-inflammatory cytokines 82 such as TGF-beta, and neurotrophic factors 83 such as BDNF. The patient may also be treated with retinoic acid or some other retinoid by administering it as a drug 84. For cytokines that may have both anti-inflammatory and pro-inflammatory capabilities, the retinoic acid biases such cytokines to exhibit their anti-inflammatory potential, as shown in the pathway labeled as 85. Pro-inflammatory cytokines, on the other hand, promote inflammation by pathways labeled as 86. Stimulation of the vagus nerve inhibits the release of pro-inflammatory cytokines 91 directly through pathways that have been described by TRACEY and colleagues. The other pathways shown in FIG. 8 to inhibit inflammation following stimulation of the vagus nerve are novel to this disclosure, and include inhibition of inflammation via anti-inflammatory cytokine pathways 92 including those that inhibit the release of pro-inflammatory cytokines 93, inhibition via neurotrophic factors 94 including those that inhibit the release of pro-inflammatory cytokines 95, and inhibition via retinoic acid pathways 96 including those that inhibit the release of pro-inflammatory cytokines 97.

It is understood that the labels in FIG. 8 that are used for simplicity to describe the pathways actually refer to a large set of related pathways. For example, the box labeled as "retinoic acid" actually refers to not only retinoic acid but also to a larger class of retinoids, as well as to retinaldehyde dehydrogenases, retinoic acid receptors (RAR), retinoid X receptors (RXR), retinoic acid response elements (RAREs), and more generally to the retinoic acid signaling system of the nervous system and related pathways.

Furthermore, it is understood that the box labeled "Anti-Inflammatory Cytokine, e.g., TGF-beta" can actually be placed within the box entitled "Neurotrophic Factor", because TFG-beta is a member of the superfamily of TGF-beta neurotrophic factors [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127]. However, because TGF-beta is ordinarily referred to simply as a cytokine, and because its anti-inflammatory competence is known to be influenced by retinoic acid, it was placed in a separate box to avoid undue confusion.

Example: Stimulation of the Vagus Nerve to Treat Alzheimer Disease

Alzheimer (or Alzheimer's) disease (AD) is the most common cause of dementia, affecting more than 5 million individuals in the United States. AD clinical decline and pathological processes occur gradually. Dementia is the end stage of many years of accumulation of pathological changes, which begin to develop decades before the earliest clinical symptoms occur. A pre-symptomatic phase occurs first, in which individuals are cognitively normal but some have AD pathological changes. This is followed by a second prodromal phase of AD, commonly referred to as mild cognitive impairment (MCI). The final phase in the evolution of AD is dementia, defined as impairments that are severe enough to produce loss of function.

Until recently, a definitive diagnosis of AD could only be made at the autopsy or by brain biopsy of an individual, by identifying amyloid plaques and neurofibrillary tangles (NFTs) in the association regions of the individual's brain, particularly in the medial aspect of the temporal lobe. Additional evidence of AD from an individual's autopsy or biopsy would include the presence of the following: the granulovacuolar degeneration of Shimkowicz, the neuropil threads of Braak, and neuronal loss with synaptic degeneration.

Amyloid precursor protein (APP) is a membrane protein that is concentrated in the synapses of neurons. APP is the precursor molecule whose proteolysis generates β-amyloid (AR), a peptide whose amyloid fibrillar form is the primary component of amyloid plaques found in the brains of AD patients.

Tau proteins, which are abundant in the central nervous system, stabilize microtubules. When tau proteins are defective and no longer stabilize microtubules properly, they can produce dementias, including AD. Defective tau protein will aggregate and twist into neurofibrillary tangles (NFTs), so that the protein is no longer available the stabilization of microtubules. As a result, the neuronal cytoskeleton falls apart, contributing to neuronal malfunction and cell death.

AD begins when cells abnormally process the amyloid precursor protein (APP), which then leads to excess production or reduced clearance of β-amyloid (AR) in the cortex. Excess of one or more forms of AR leads to a cascade, characterized by abnormal tau protein aggregation, synaptic dysfunction, cell death, and brain shrinkage. The detailed molecular mechanism of tau protein aggregation is unknown, but it is thought that extracellular deposits of AR in the brains of AD patients promote tau polymerization.

Inflammation and the immune system play a significant role in AD pathogenesis. The inflammatory components in AD include microglia and astrocytes, the complement system, and various inflammatory mediators (including cytokines and chemokines). Microglia are the resident immune cell types of the central nervous system, and in AD, microglia may cause damage by secretion of neurotoxins. When microglia become activated during inflammation, they also secrete a variety of inflammatory mediators including cytokines (TNF and interleukins IL-1β and IL-6) and chemokines (macrophage inflammatory protein MIP-1a, monocyte chemoattractant protein MCP-1 and interferon inducible protein IP-10) that promote the inflammatory state.

Microglia accumulate in locations that contain AR and are associated with the local toxicity of AR plaques. Whether the accumulated microglia contribute to the removal or deposition of plaque is now thought to depend on the detailed microenvironment of the accumulated microglia. Microglial cell activation and migration toward β-amyloid plaques precede the appearance of abnormally shaped neurites and the formation of neurofibrillary tangles. It has been shown that following microglial migration to the plaques, microglial-derived proinflammatory cytokine TNF-alpha is induced, which in turn induces accumulation of the aggregation-prone tau molecules in neurites via reactive oxygen species. [GORLOVY, P., Larionov, S., Pham, T. T. H., Neumann, H. Accumulation of tau induced in neurites by microglial proinflammatory mediators. FASEB J. 23, 2502-2513 (2009)]. Elevated levels of TNF-alpha also induce an increased expression of interleukin-1, which in turn increases production of the precursors that may be necessary for formation of β-amyloid plaques and neurofibrillary tangles. Thus, the secretion of TNF-alpha by microglia contributes to a cycle wherein tau aggregates to form tangles, R-amyloid plaques are formed, microglia aggregate to those plaques, and more TNF-alpha is secreted by microglia cells.

In addition to its proinflammatory functions, TNF-alpha is a gliotransmitter that regulates synaptic function in neural networks. In particular, TNF-alpha has been shown to mediate the disruption in synaptic memory mechanisms. Etanercept, a biologic antagonist of TNF-alpha, when delivered by perispinal administration, has been shown to improve the cognitive abilities of AD patients, even within minutes of its administration [Edward L TOBINICK and Hyman Gross. Rapid cognitive improvement in Alzheimer disease following perispinal etanercept administration. Journal of Neuroinflammation 2008, 5:2; W Sue T GRIFFIN. Perispinal etanercept: Potential as an Alzheimer therapeutic. Journal of Neuroinflammation 2008, 5:3; Edward TOBINICK. Tumour Necrosis Factor Modulation for Treatment of Alzheimer's Disease Rationale and Current Evidence. CNS Drugs 2009; 23 (9): 713-725]. Furthermore, in a population of adults with rheumatoid arthritis, CHOU et al. observed that the risk of AD was significantly reduced by TNF inhibitor therapy for the rheumatoid arthritis, but not by other disease modifying agents used for treatment of rheumatoid arthritis. It may therefore be concluded that TNF may be an important component in the pathogenesis of AD [Richard C. CHOU, Michael A. Kane, Shiva Gautam and Sanjay Ghirmire. Tumor Necrosis Factor Inhibition Reduces the Incidence of Alzheimer's Disease in Rheumatoid Arthritis Patients. Program abstracts of the American College of Rheumatology/Association of Rheumatology Health Professionals Scientific Meeting, Nov. 8, 2010, Atlanta Ga., Presentation No. 640].

With the ability to better stage the progression of AD through use of biomarkers, treatment of AD may be justified at stages prior to actual dementia. With a better understanding of the pathogenesis of AD, those treatments might be directed to slowing, stopping, or reversing the pathophysiological processes underlying AD.

Biomarkers are cognitive, physiological, biochemical, and anatomical variables that can be measured in a patient that indicate the progression of AD. The most commonly measured biomarkers are decreased Aβ42 in the cerebrospinal fluid (CSF), increased CSF tau, decreased fluorodeoxyglucose uptake on PET (FDG-PET), PET amyloid imaging, and structural MRI measures of cerebral atrophy. Biomarkers of Aβ deposition become abnormal early, before neurodegeneration and clinical symptoms occur. Biomarkers of neuronal injury, dysfunction, and neurodegeneration become abnormal later in the disease. Cognitive symptoms are directly related to biomarkers of neurodegeneration, rather than to biomarkers of Aβ deposition.

At the present time, other than physical and mental exercise, only symptomatic therapies for AD are available. All approved drugs for the symptomatic treatment of AD modulate neurotransmitters—either acetylcholine or glutamate: cholinesterase inhibitors and partial N-methyl-D-aspartate antagonists. Psychotropic medications are also used to treat secondary symptoms of AD such as depression, agitation, and sleep disorders.

Therapies directed to modifying AD progression itself are considered investigational. These include treatment of the intense inflammation that occurs in the brains of patients with AD, estrogen therapy, use of free-radical scavengers, therapies designed to decrease toxic amyloid fragments in the brain (vaccination, anti-amyloid antibodies, selective amyloid-lowering agents, chelating agents to prevent amyloid polymerization, brain shunting to improve removal of amyloid, and beta-secretase inhibitors to prevent generation of the A-beta amyloid fragment), and agents that may prevent or reverse excess tau phosphorylation and thereby diminish formation of neurofibrillary tangles.

However, it is increasingly recognized that a single target or pathogenic pathway for the treatment of AD is unlikely to be identified. The best strategy is a multi-target therapy that includes multiple types of treatments [Mangialasche F, Solomon A, Winblad B, Mecocci P, Kivipelto M. Alzheimer disease: clinical trials and drug development. Lancet Neurol. 2010 July; 9(7):702-16]. Targets in that multi-target approach will include inflammatory pathways, and several therapeutic agents have been proposed to target them—nonsteroidal anti-inflammatory drugs, statins, RAGE antagonists and antioxidants [Stuchbury G, Munch G. Alzheimer associated inflammation, potential drug targets and future therapies. J Neural Transm. 2005 March; 112(3): 429-53]. Another such agent, Etanercept, was mentioned above as targeting TNF-alpha, but its use has the disadvantage that because it does not pass the blood-brain barrier (BBB), its administration is via a painful spinal route or via an experimental method to get through the BBB [U.S. Pat. No. 7,640,062, entitled Methods and systems for management of alzheimer's disease, to SHALEV]. One TNF-inhibitor that does not have this disadvantage is thalidomide [Tweedie D, Sambamurti K, Greig N H: TNF-alpha Inhibition as a Treatment Strategy for Neurodegenerative Disorders: New Drug Candidates and Targets. Curr Alzheimer Res 2007, 4(4):375-8]. However, thalidomide is well known by the public to cause birth defects, and in a small trial, its use did not appear to improve cognition in AD patients [Peggy PECK. IADRD: Pilot Study of Thalidomide for Alzheimer's Disease Fails to Detect Cognitive Benefit but Finds Effect on TNF-alpha. Doctor's Guide Global Edition, Jul. 26, 2002]. There is therefore a need in the art for new therapies that target TNF-alpha, including its physiological activity for a given amount, as a component of a multi-target approach to treating AD In 2002, it was reported that electrical stimulation of the vagus nerve has a beneficial effect on cognition in patients with AD [Sjögren M J, Hellström P T, Jonsson M A, Runnerstam M, Silander H C, Ben-Menachem E. Cognition-enhancing effect of vagus nerve stimulation in patients with Alzheimer's disease: a pilot study. J Clin Psychiatry. 2002 November; 63(11):972-80]. The rationale for the trial was that vagus nerve stimulation had previously been found to enhance the cognitive abilities of patients that were undergoing vagus nerve stimulation for other conditions such as epilepsy and depression, as well cognitive abilities observed in animal studies. Results concerning the AD patients' improved cognitive abilities over a longer period of time, along with improvement in tau protein of cerebrospinal fluid, were subsequently reported [Merrill C A, Jonsson M A, Minthon L, Ejnell H, C-son Silander H, Blennow K, Karlsson M, Nordlund A, Rolstad S, Warkentin S, Ben-Menachem E, Sjögren M J. Vagus nerve stimulation in patients with Alzheimer's disease: Additional follow-up results of a pilot study through 1 year. J Clin Psychiatry. 2006 August; 67(8):1171-8]. Stimulation of the vagus nerve to treat dementia might be more effective than stimulation of nerves found in locations such as the spine, forehead, and earlobes [Cameron M H, Lonergan E, Lee H. Transcutaneous Electrical Nerve Stimulation (TENS) for dementia. Cochrane Database of Systematic Reviews 2003, Issue 3. Art. No.: CD004032. (2009 update)]. The method of using vagal nerve stimulation to treat AD had been disclosed earlier in U.S. Pat. No. 5,269,303, entitled Treatment of dementia by nerve stimulation, to WERNICKE et al., but neither that patent nor the clinical trials proposed any physiological intermediary through which vagal nerve stimulation may result in clinical improvement to AD patients.

It has been proposed that electrical stimulation of the vagus nerve may attenuate an inflammatory response. In particular, methods involving electrical stimulation of the vagus nerve have been disclosed for attenuating or inhibiting the release of the pro-inflammatory cytokine TNF-alpha, including AD as one disease in a long list of diseases involving inflammation [U.S. Pat. No. 6,610,713 and U.S. Pat. No. 6,838,471, entitled Inhibition of inflammatory cytokine production by cholinergic agonists and vagus nerve stimulation, to TRACEY; Kevin J. TRACEY. The inflammatory reflex. Nature 420 (2002): 853-859; Kevin J. TRACEY. Physiology and immunology of the cholinergic anti-inflammatory pathway. J. Clin. Invest. 117 (2007):289-296]. It has also been proposed that electrical stimulation of nerves of the sympathetic nervous system (particularly the splenic nerve) may also attenuate an inflammatory response, by attenuating or inhibiting the release of TNF-alpha, including AD as a one disease in a long list of diseases involving inflammation [U.S. Pat. No. 7,769,442, entitled Device and method for inhibiting release of pro-inflammatory mediator, to SHAFER]. PROLO et al. noted the above-mention vagal nerve stimulation investigations and predicted that interventions based on attenuation of inflammation would be useful for the treatment of AD [Paolo PROLO, Francesco Chiappelli, Alberto Angeli, Andrea Dovio, Maria Luisa Sartori, Fausto Fanto, Negoita Neagos, Ercolano Manfrini. Putative Neurolmmune Mechanisms in Alzheimer's Disease: Modulation by Cholinergic Anti-Inflammatory Reflex (CAIR). International Journal of Integrative Biology 2007, Vol 1 (No. 2):88-95].

However, as noted above, TNF-alpha is involved in more than inflammation in AD [Ian A. CLARK, Lisa M. Alleva and Bryce Vissel. The roles of TNF in brain dysfunction and disease. Pharmacology & Therapeutics, 128 (Issue 3, December 2010): 519-548]. It is also a gliotransmitter that regulates synaptic function in neural networks [Gertrudis PEREA and Alfonso Araque. GLIA modulates synaptic transmission. Brain Research Reviews. 63 (Issues 1-2, May 2010):93-102]. In that capacity, TNF-alpha has been shown to mediate the disruption in synaptic memory mechanisms. None of the above-mentioned citations have proposed that stimulation of the vagus nerve modulates the capacity of TNF-alpha to function as a gliotransmitter, which can be released from any glial cell, including oligodendrocytes, astrocytes, and microglia. Such modulation in capacity can be due to a change in the amount of TNF-alpha or in the activity of a given amount of TNF-alpha or in the activity of the cells between which TNF-related gliotransmission occurs. In fact, the above-mentioned citations are concerned only with the attenuation or inhibition of the release of TNF-alpha as a pro-inflammatory mediator, but not with its degradation or modification or with changes in its activity for a given amount.

Stimulation of the vagus nerve may also antagonize the pro-inflammatory capabilities of TNF-alpha and other pro-inflammatory cytokines through mechanisms that are different from those proposed by TRACEY and colleagues. In particular, it has been observed that stimulation of the vagus nerve may enhance the release of retinoic acid (RA) from nerve locations that produce RA from retinaldehyde using retinaldehyde dehydrogenases [van de PAVERT SA, Olivier B J, Goverse G, Vondenhoff M F, Greuter M, Beke P, Kusser K, Höpken U E, Lipp M, Niederreither K, Blomhoff R, Sitnik K, Agace W W, Randall T D, de Jonge W J, Mebius R E. Chemokine CXCL13 is essential for lymph node initiation and is induced by retinoic acid and neuronal stimulation. Nat Immunol. 10(11, 2009): 1193-1199]. The retinoic acid so released may directly inhibit the release or functioning of proinflammatory cytokines, which would be an anti-pro-inflammatory mechanism that is distinct from the one proposed by TRACEY and colleagues [Malcolm Maden. Retinoic acid in the development, regeneration and maintenance of the nervous system. Nature Reviews Neuroscience 8 (2007), 755-765]. Because RA strongly suppresses the production of IL6, inhibits amyloid-beta-induced TNF-alpha production, and inhibits expression of inducible NO synthase (iNOS) in activated microglia, the release of RA following stimulation of the vagus nerve will also serve to inhibit inflammation [K. SHUDO, H. Fukasawa, M. Nakagomi and N. Yamagata. Towards Retinoid Therapy for Alzheimer's Disease. Current Alzheimer Research, 2009, 6, 302-311]. Retinoic acid can also regulate the expression of the tau protein, and in particular the level of phosphorylated forms of tau [Andrea MALASPINA and Adina T. Michael-Titus. Is the modulation of retinoid and retinoid associated signaling a future therapeutic strategy in neurological trauma and neurodegeneration? J. Neurochem. (2008) 104, 584-595]. Furthermore, stimulation of nerves to release retinoic acid or activate its receptors may also promote the clearance of beta amyloids in AD by RA activation of the heterodimeric complex formed by PPAR-RXR [Camacho I. E., Serneels L., Spittaels K., Merchiers P., Dominguez D. and De Strooper B. Peroxisome-proliferator-activated receptor gamma induces a clearance mechanism for the amyloid-beta peptide. J. Neurosci. 24 (2004), 10908-10917].

The cytokine TGF-beta acts in a highly contextual manner, and depending on cell type and environment, TGF-beta may promote cell survival or induce apoptosis, stimulate cell proliferation or induce differentiation, and initiate or resolve inflammation. In the presence of RA, TGF-beta is biased towards anti-inflammation, so the release of RA following vagal nerve stimulation may inhibit inflammation by that pro-anti-inflammatory mechanism as well [Tony Wyss-Coray. TGF-beta Pathway as a Potential Target in Neurodegeneration and Alzheimer's. Current Alzheimer Research, 3 (2006): 191-195]. Treating the patient with oral retinoic acid may also promote an anti-inflammatory bias for TGF-beta. Furthermore, vagal nerve stimulation may also stimulate the production of the TGF-beta that can act as an anti-inflammatory agent [CORCORAN, Ciaran; Connor, Thomas J; O'Keane, Veronica; Garland, Malcolm R. The effects of vagus nerve stimulation on pro- and anti-inflammatory cytokines in humans: a preliminary report. Neuroimmunomodulation 12 (5, 2005): 307-309].

TGF-beta is a member of the TGF-beta superfamily of neurotrophic factors. Neurotrophic factors serve as growth factors for the development, maintenance, repair, and survival of specific neuronal populations, acting via retrograde signaling from target neurons by paracrine and autocrine mechanisms. Nerve growth factor (NGF) is the most widely examined neurotrophin in experimental models of AD, and of all the factors tested, NGF appears to be the most effective in improving the survival and maintenance of cholinergic neurons. It is therefore considered to be a promising therapeutic agent for AD [Yossef S. LEVY, Yossi Gilgun-Sherki, Eldad Melamed and Daniel Offen. Therapeutic Potential of Neurotrophic Factors in Neurodegenerative Diseases. Biodrugs 2005; 19 (2): 97-127; Mark H. TUSZYNSKI. Nerve Growth Factor Gene Therapy in Alzheimer Disease. Alzheimer Dis Assoc Disord 21 (2, 2007): 179-189]. However, major problems in using neurotrophic factors for therapy are their inability to cross blood-brain-barrier, adverse effects resulting from binding to the receptor in other organs of the body and their low diffusion rate.

It is known that vagal nerve stimulation and transcranial magnetic stimulation can increase the levels of at least one neurotrophic factor in the brain, brain-derived neurotrophic factor (BDNF), which has been studied extensively in connection with the treatment of depression. However, it has never been suggested that vagal nerve stimulation may be utilized to increase BDNF levels in AD patients. BDNF is known to be reduced in AD brains, and the introduction of BDNF into the brain of animal models of AD promotes regeneration [Alan H NAGAHARA et al. Neuroprotective effects of brain-derived neurotrophic factor in rodent and primate models of Alzheimer's disease. Nat Med. 15(3, 2009): 331-337]. Vagal nerve stimulation may likewise promote the expression of other neurotrophic factors such as NGF, which circumvents the problem of blood-brain barrier blockage [Follesa P, Biggio F, Gorini G, Caria S, Talani G, Dazzi L, Puligheddu M, Marrosu F, Biggio G. Vagus nerve stimulation increases norepinephrine concentration and the gene expression of BDNF and bFGF in the rat brain. Brain Research 1179 (2007): 28-34; Biggio F, Gorini G, Utzeri C, 011a P, Marrosu F, Mocchetti I, Follesa P. Chronic vagus nerve stimulation induces neuronal plasticity in the rat hippocampus. Int J. Neuropsychopharmacol. 12(9, 2009): 1209-21; Roberta Zanardini, Anna Gazzoli, Mariacarla Ventriglia, Jorge Perez, Stefano Bignotti, Paolo Maria Rossini, Massimo Gennarelli, Luisella Bocchio-Chiavetto. Effect of repetitive transcranial magnetic stimulation on serum brain derived neurotrophic factor in drug resistant depressed patients. Journal of Affective Disorders 91 (2006) 83-86]. Patent application US20100280562, entitled Biomarkers for monitoring treatment of neuropsychiatric diseases, to PI et al, disclosed the measurement of BDNF following vagal nerve stimulation. However, that application is concerned with the search for biomarkers involving the levels of BDNF, rather than a method for treating a neurodegenerative disease using vagal nerve stimulation.

Magnetic stimulation of AD patients has been performed, but its use has been intended to affect cognitive skills using transcranial magnetic stimulation [Mamede de Carvalho, Alexandre de Mendonça, Pedro C. Miranda, Carlos Garcia and Maria Lourdes Sales Luis. Magnetic stimulation in Alzheimer's disease. Journal of Neurology 244 (1997, 5): 304-307; Cotelli M, Manenti R, Cappa S F, Zanetti O, Miniussi C. Transcranial magnetic stimulation improves naming in Alzheimer disease patients at different stages of cognitive decline. Eur J. Neurol. 15(12, 2008):1286-92; Guse B, Falkai P, Wobrock T. Cognitive effects of high-frequency repetitive transcranial magnetic stimulation: a systematic review. J Neural Transm. 117(1, 2010):105-22].

Accordingly, methods are disclosed here to treat AD patients, preferably as part of a multi-target therapy. The foregoing review of AD disclosed six novel mechanisms by which stimulation of the vagus nerve may be used to treat AD: (1) stimulate the vagus nerve in such a way as to enhance the availability or effectiveness of TGF-beta or other anti-inflammatory cytokines; (2) stimulate the vagus nerve in such a way as to enhance the availability or effectiveness of retinoic acid; (3) stimulate the vagus nerve in such a way as to promote the expression of the neurotrophic factors such as BDNF; (4) stimulate the vagus nerve to modulate the capacity of TNF-alpha to function as a gliotransmitter, including modulating the activity of the cells between which TNF-related gliotransmission occurs; (5) stimulate the vagus nerve in such a way as to suppress the release or effectiveness of pro-inflammatory cytokines, through a mechanism that is distinct from the one proposed by TRACEY and colleagues; (6) stimulate the vagus nerve to modulate the degradation of TNF-alpha, and/or modify the activity of existing TNF-alpha molecules as a pro-inflammatory mediator.

In the preferred embodiment, the method stimulates the vagus nerve as indicated in FIGS. 6 and 7, using the toroidal magnetic stimulation device that is disclosed herein. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed repeatedly, e.g., once a week for six months. However, parameters of the stimulation may be varied in order to obtain a beneficial response, as indicated, for example, by the measurement of levels and/or activities of TGF-beta, neurotrophic factors, retinoic acid, and/or TNF-alpha in the patient's peripheral circulation and/or in the patient's cerebrospinal fluid, during and subsequent to each treatment.

Example: Stimulation of the Vagus Nerve to Treat Parkinson's Disease

Parkinson's disease (PD) is a chronic neurodegenerative disease that is characterized by problems with movement, particularly tremor at rest, slowness of gait, joint and muscle rigidity, and unstable posture. The disease is also commonly accompanied by cognitive, autonomic, and sensory dysfunctions. PD symptoms result from dopamine insufficiency in dopaminergic neurons of the substantia nigra and other portions of the midbrain. In PD, neuromelanin-pigmented, dopamine-secreting neurons in those regions die, at locations where there is an abnormal accumulation and aggregation of misfolded alpha-synuclein protein in the form of so-called Lewy bodies.

Definite diagnosis of PD is made only at autopsy with a finding of substantial nerve cell depletion with accompanying gliosis in the substantia nigra, of at least one Lewy body in the substantia nigra or in the locus coeruleus, and of no pathological evidence for other diseases that produce symptoms of Parkinsonism. Diagnosis of PD based upon symptoms alone is considered to be only probable, with up to 20% of the probable PD diagnoses not confirmed after autopsy. The onset and progression of probable PD in an individual is commonly quantified using a scoring device known as the Unified Parkinson's Disease Rating Scale (UPDRS), which incorporates considerations used to diagnose PD. The scoring of symptoms follows standard neurological examination practice, in which finding of the following contribute to the diagnosis of PD—tremor (especially if more pronounced at rest); slowing of motion and muscle rigidity; onset of symptoms on only one side of the body; and improvement with administration of levodopa [J JANKOVIC. Parkinson's disease: clinical features and diagnosis. J Neurol Neurosurg Psychiatry 79 (2008):368-376; Christopher G. GOETZ et al. Movement Disorder Society-Sponsored Revision of the Unified Parkinson's Disease Rating Scale (MDS-UPDRS): Scale Presentation and Clinimetric Testing Results. Movement Disorders 23 (No. 15, 2008): 2129-2170].

Currently, there are no laboratory tests that can confirm a neurological diagnosis of probable PD. Blood and cerebrospinal fluid tests of PD patients are often normal, electroencephalography is not able to detect PD, and the MRI and CAT scans of PD patients appear normal. However, experimental biomarkers for diagnosing PD are available [A. W. Michell, S. J. G. Lewis, T. Foltynie and R. A. Barker. Biomarkers and Parkinson's disease. Brain (2004), 127, 1693-1705; Manuel B. Graeber. Biomarkers for Parkinson's disease. Experimental Neurology 216 (2009) 249-253].

PD is the second most common neurodegenerative disease after Alzheimer's disease and is the most common movement disorder. Some movement disorders resemble PD but belong to a more general category of disorder referred to as Parkinsonian syndrome or Parkinsonism. Other movement disorders may involve neurodegeneration at some point in their pathogenesis, including multiple system atrophy, progressive supranuclear palsy, corticobasal degeneration, tremor, dystonia (including torticollis, spasmodic dysphonia and blepharospasm), restless leg syndrome, tic and Tourette syndrome, chorea, spasticity and tardive dyskinesia. It is understood that the methods disclosed herein for the treatment of PD may be used to treat such other movement disorders as well.

PD usually appears in people between 40 and 70 years of age, with the incidence of PD peaking in people in their sixties. More than one million individuals in the North America have PD, and in industrialized societies, greater than 1% of the population over the age of 65 years have the disease. Increasing age beyond 60 years is a strong risk factor for PD. Currently, there is no clear evidence that PD is found preferentially in a particular sex or geographical location. Exposure to the neurotoxin MPTP causes permanent symptoms that are similar to those in PD, and exposure to toxic chemicals such as pesticides (e.g., rotenone), herbicides (e.g., paraquat), and fungicides (e.g., maneb) greatly increase the risk of developing PD. Only 5-15% of the cases of PD are related to the patient having a predisposing gene, but some such genes lead to early-onset PD. Use of tobacco, coffee, non-steroidal anti-inflammatory drugs and calcium channel blocker drugs have been found to protect against PD. [Lonneke M L DELAU, Monique M B Breteler. Epidemiology of Parkinson's disease. Lancet Neurol 5 (2006): 525-35; SHIN, J.-H., V. L. Dawson, T. M. Dawson, SnapShot: Parkinson's disease pathogenesis. Cell 139 (2009): 440-440].

BRAAK and colleagues present evidence that PD ordinarily begins in the dorsal motor nucleus of the vagus nerve (in the medulla) and not in the midbrain dopaminergic neurons as has been generally assumed. Furthermore, since this site is connected to the periphery by the vagus nerve, they propose that toxic factors enters the central nervous system via the vagus nerve, and the pathological process then progresses up the neuroaxis, during which components of the olfactory, autonomic, limbic, and somatomotor systems become progressively involved [BRAAK H, Bohl J R, Muller C M, Rub U, de Vos R A, Del Tredici K., Stanley Fahn Lecture 2005: The staging procedure for the inclusion body pathology associated with sporadic Parkinson's disease reconsidered. Mov Disord 2006; 21(12):2042-51]. Accordingly, methods for preventing or treating PD are to stimulate the vagus nerve in such a way as to prevent toxins (environmental toxin, virus, or alpha-synuclein clusters) from reaching the dorsal motor nucleus of the vagus nerve, to serve as an antidote to toxins that have already reached that location, and to prevent the pathology from progressing up the neuroaxis.

The pathophysiological origins of dopaminergic nerve depletion in the substantia nigra of PD patients are thought to involve mitochondrial dysfunction, oxidative and nitrosative stress, and impairment of the ubiquitinproteasome system (UPS) and the autophagy-lysosome pathway (ALP), with attendant aberrant protein handling. Nerve depletion occurs in dopamine producing cells of the substantia nigra because those cell are uniquely susceptible to damage, as a result of their high energy requirements and their expression of a unique Cav 1.3 calcium channel protein. The calcium channel protein causes sustained elevations in cytosolic calcium concentration, particularly in dendrites, which stimulates mitochondrial respiratory metabolism and generates reactive oxygen species (ROS). Generation of ROS or damage from environmental toxins leads to inhibition of the first enzyme complex of the mitochondrial electron-transfer chain (mitochondrial complex I). For example, the Parkinson-producing toxin MPTP specifically inhibits mitochondrial complex I. This leads to eventual depolarization of the mitochondrial membrane and opening of the mitochondrial permeability transition pore. A by-product of such mitochondrial impairment is increased production of more ROS, producing a vicious cycle of more oxidative damage within the neurons of PD patients [Chan C S, Guzman J N, Ilijic E, Mercer J N, Rick C, Tkatch T, Meredith G E, Surmeier D J (2007) 'Rejuvenation' protects neurons in mouse models of Parkinson's disease. Nature 447: 1081-1086].

Alpha-synuclein (alpha-SN) is a cytoplasmic protein that is highly expressed in dopaminergic neuronal cells and that interacts with pre-synaptic membranes, suggesting that its function is to regulate synaptic vesicle pools, including control of dopamine levels. As noted above, alpha-SN deposits in the form of Lewy Bodies are a defining characteristic of PD. Oxidation and nitration of alpha-SN in the environment of dysfunctional mitochondria lead to the formation of alpha-SN aggregates and the stabilization of assembled alpha-SN filaments. Such abnormal alpha-SN might also damage mitochondria directly, contributing to even greater oxidative stress and mitochondrial dysfunction. The conversion of alpha-SN from soluble monomers to aggregated amyloid-like insoluble forms is a key event in PD pathogenesis.

Protein mishandling due to dysfunction in the ubiquitin-proteasome system (UPS) and the autophagy-lysosome pathway (ALP) are major pathways leading to neuronal degeneration in PD. The UPS pathway targets and rapidly destroy misfolded proteins in cells, through attachment of ubiquitin to target proteins. The ubiquitin tag serves as a signal for their degradation by a proteasome, which is an abundant ATP-dependent protease. The second pathway is autophagy, which is a catabolic process involving the degradation of a cell's own components through lysosomal machinery. It comprises several types: macroautophagy, microautophagy, and chaperone-mediated autophagy. Although the UPS and ALP pathways may clear damaged cell components in early stages of PD, eventually they may themselves become damaged and contribute to the progression of PD.

Abnormal alpha-SN is thought to cause UPS dysfunction through binding and inhibiting the 20/26S proteasome, and abnormal or aggregated forms of alpha-SN may also overwhelm the degradative capacity of the proteasome, leading to UPS impairment beyond that which is attributable to oxidation of UPS components.

Once the UPS has become dysfunctional, autophagy is upregulated as a compensatory mechanism for degrading aggregated, misfolded and abnormal proteins. However, lysosomal malfunction has been found to accompany alpha-SN aggregation, supporting the view that ALP dysfunction is an important mechanism of neurodegeneration. Furthermore, dysfunction of the ALP is thought to occur naturally as a consequence of aging, so that clearance of aggregating alpha-SN might fail in the cells of elderly individuals irrespective of whether the abnormal alpha-SN promotes ALP dysfunction.

Autophagy has a dual role: to promote cell survival through removal of abnormal cellular components, and to promote cell death when intracellular damage is beyond repair. Inappropriate or prolonged activation of autophagy may therefore lead to the complete death and destruction of some cells in PD. Other mechanisms for the death of the defective dopamine-producing cells include caspase-dependent and caspase-independent pathways, endoplasmic-reticulum stress, neuronal nitric oxide synthase (nNOS) activation, DNA damage, poly(ADP-ribose) polymerase (PARP) activation, and GAPDH modification [Dale E. BREDESEN, Rammohan V. Rao and Patrick Mehlen. Cell death in the nervous system. Nature 443(7113, 2006):796-802; Tianhong PAN, Seiji Kondo, Weidong Le, Joseph Jankovic. The role of autophagy-lysosome pathway in neurodegeneration associated with Parkinson's disease. Brain 131 (2008): 1969-1978].

Another mechanism leading to the death of dopamine-producing cells in PD is inflammatory, through microglial activation. The activation begins with microglia detecting stimulatory signaling molecules such as the active form of MMP-3, alpha-SN and neuromelanin that have leaked from intact cells or that are extracellular after the destruction of dopamine-producing cells by mechanisms that were described above. Activated microglia cause dopamine neuronal degeneration either by superoxide, NO and other proinflammatory cytokines or by direct phagocytosis against neurons that are in the process of becoming dysfunctional or even normal (bystander) neurons. Products derived from microglia and astrocytes act in a combinatorial manner to promote neurotoxicity. The inflammatory response becomes a vicious cycle because additional microglial activating factors are leaked or released from the cells that are attacked during the inflammation [Kim Y S, Joh T H. Microglia, major player in the brain inflammation: their roles in the pathogenesis of Parkinson's disease. Exp Mol Med 38 (2006): 333-347].

Neutralizing the proinflammatory cytokine tumor necrosis factor (TNF-alpha) has been found to reduce nigral degeneration in an animal model of PD. [Melissa K. McCOY, Terina N. Martinez, Kelly A. Ruhn, David E. Szymkowski, Christine G. Smith, Barry R. Botterman Keith E. Tansey and Malù G. Tansey. Blocking Soluble Tumor Necrosis Factor Signaling with Dominant-Negative Tumor Necrosis Factor Inhibitor Attenuates Loss of Dopaminergic Neurons in Models of Parkinson's Disease. The Journal of Neuroscience 26(37, 2006):9365-9375]. U.S. Pat. No. 6,610,713 and U.S. Pat. No. 6,838,471, entitled Inhibition of inflammatory cytokine production by cholinergic agonists and vagus nerve stimulation, to TRACEY, also suppress the release of proinflammatory cytokines, such as TNF-alpha, by vagal nerve stimulation. The methods described in those patents might therefore substitute for the anti-TNF treatment that was used by McCOY and colleagues. However, there is no mention or suggestion that the methods described in those patents are intended to modulate the activity of anti-inflammatory cytokines such as TGF-beta or to antagonize TNF-alpha by some other mechanism. One such mechanism involves the release of retinoic acid from cells [Malcolm Maden. Retinoic acid in the development, regeneration and maintenance of the nervous system. Nature Reviews Neuroscience 8 (2007), 755-765] and is discussed below.

Under normal physiologic conditions, microglia are maintained quiescent by the coordinate action of neurons and astrocytes. Astrocytes are able to suppress microglial activation by releasing TGF-beta or IL-10 [Vincent V A, Tilders F J, Van Dam A M. Inhibition of endotoxin-induced nitric oxide synthase production in microglial cells by the presence of astroglial cells: a role for transforming growth factor beta. Glia. 1997 March; 19(3):190-8]. TGF-beta is also produced by, and promotes the survival of, neurons in the substantia nigra and the striatum [Kerstin Krieglstein. Factors promoting survival of mesencephalic dopaminergic neurons. Cell Tissue Res (2004) 318: 73-80].

The orphan nuclear receptor Nurr1 also inhibits expression of proinflammatory neurotoxic mediators in microglia and astrocytes. A heterodimer between the retinoid X receptor and Nurr1 also rescues dopamine-producing neurons from degeneration [Stina Friling, Maria Bergsland and Susanna Kjellander. Activation of Retinoid X Receptor increases dopamine cell survival in models for Parkinson's disease. BMC Neuroscience 2009, 10:146; Kaoru Saijo, Beate Winner, Christian T. Carson, Jana G. Collier, Leah Boyer, Michael G. Rosenfeld, Fred H. Gage, and Christopher K. Glass. A Nurr1/CoREST Pathway in Microglia and Astrocytes Protects Dopaminergic Neurons from Inflammation-Induced Death. Cell 137, 47-59, Apr. 3, 2009].

This implicates retinoic acid in the response to inflammatory and other damage through the following mechanism. Retinoic acid acts by binding to heterodimers of the retinoic acid receptor (RAR) and the retinoid X receptor (RXR), which then bind to retinoic acid response elements (RAREs) to activate transcription in the regulatory regions of target survival and repair genes. Retinoic acid signaling is also involved in normal nigrostriatal functioning, as evidenced by the fact that disulphiram, which blocks the synthesis of retinoic acid, induces Parkinsonism by producing lesions. The dopaminergic neurons of the nigrostriatal system contain high levels of retinaldehyde dehydrogenase that generate retinoic acid in the axon terminals, which in turn acts on neurotransmission in an autocrine fashion or on the striatal cells in a paracrine fashion [Malcolm Maden. Retinoic acid in the development, regeneration and maintenance of the nervous system Nature Reviews Neuroscience 8 (2007), 755-765].

Thus, the enhanced availability of TGF-beta and retinoic acid are thought to have anti-inflammatory effects in PD, and both have been reported to be enhanced by stimulation of the vagus nerve [CORCORAN, Ciaran; Connor, Thomas J; O'Keane, Veronica; Garland, Malcolm R. The effects of vagus nerve stimulation on pro- and anti-inflammatory cytokines in humans: a preliminary report. Neuroimmunomodulation 12 (5, 2005): 307-309; van de PAVERT S A, Olivier B J, Goverse G, Vondenhoff M F, Greuter M, Beke P, Kusser K, Höpken U E, Lipp M, Niederreither K, Blomhoff R, Sitnik K, Agace W W, Randall T D, de Jonge W J, Mebius R E. Chemokine CXCL13 is essential for lymph node initiation and is induced by retinoic acid and neuronal stimulation. Nat Immunol. 10(11, 2009): 1193-1199].

TGF-beta is a member of the TGF-beta superfamily of neurotrophic factors. Neurotrophic factors serve as growth factors for the development, maintenance, repair, and survival of specific neuronal populations, acting via retrograde signaling from target neurons by paracrine and autocrine mechanisms. Other neurotrophic factors, such as glial cell line-derived neurotrophic factor (GDNF) and neurturin also strongly promote the survival of dopamine-producing neurons. However, major problems in using neurotrophic factors for therapy are their inability to cross blood-brain-barrier, adverse effects resulting from binding to the receptor in other organs of the body and their low diffusion rate. A recently discovered neurotrophic factor, mesencephalic astrocyte-derived neurotrophic factor (MANF), is able to diffuse more rapidly but is also unable to cross the blood-brain barrier [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127; Voutilainen M H, Bäck S, Pörsti E, Toppinen L, Lindgren L, Lindholm P, Peränen J, Saarma M, Tuominen R K. Mesencephalic Astrocyte-Derived Neurotrophic Factor Is Neurorestorative in Rat Model of Parkinson's Disease. The Journal of Neuroscience, Jul. 29, 2009, 29(30):9651-9659].

However, it is known that vagal nerve stimulation and transcranial magnetic stimulation can increase the levels of at least one neurotrophic factor in the brain, brain-derived neurotrophic factor (BDNF), which has been studied extensively in connection with the treatment of depression. It is therefore possible that vagal nerve stimulation may likewise promote the expression of the neurotrophic factors such as GDNF and MANF that are known to promote the survival of dopamine-producing cells in PD, thereby circumventing the problem of blood-brain barrier blockage [Follesa P, Biggio F, Gorini G, Caria S, Talani G, Dazzi L, Puligheddu M, Marrosu F, Biggio G. Vagus nerve stimulation increases norepinephrine concentration and the gene expression of BDNF and bFGF in the rat brain. Brain Research 1179 (2007): 28-34; Biggio F, Gorini G, Utzeri C, 011a P, Marrosu F, Mocchetti I, Follesa P. Chronic vagus nerve stimulation induces neuronal plasticity in the rat hippocampus. Int J. Neuropsychopharmacol. 12(9, 2009):1209-21; Roberta Zanardini, Anna Gazzoli, Mariacarla Ventriglia, Jorge Perez, Stefano Bignotti, Paolo Maria Rossini, Massimo Gennarelli, Luisella Bocchio-Chiavetto. Effect of repetitive transcranial magnetic stimulation on serum brain derived neurotrophic factor in drug resistant depressed patients. Journal of Affective Disorders 91 (2006) 83-86]. Patent application US20100280562, entitled Biomarkers for monitoring treatment of neuropsychiatric diseases, to PI et al, disclosed the measurement of GDNF following vagal nerve stimulation. However, that application is concerned with the search for biomarkers involving the levels of GDNF, rather than a method for treating a neurodegenerative disease using vagal nerve stimulation.

It is known that the levels of BDNF are rapidly regulated by sensory input during development and in adulthood, particularly the presence or absence of bright light [Eero CASTREN, Francisco Zafra, Hans Thoenen, and Dan Lindholm. Light regulates expression of brain-derived neurotrophic factor mRNA in rat visual cortex. Proc. Nad. Acad. Sci. USA 89 (1992): 9444-9448]. The levels of other neurotrophic factors may also be regulated by sensory input. Accordingly, it may be possible to enhance the effect of vagal nerve stimulation on the levels of neurotrophic factors by simultaneously presenting the waveform of the vagal nerve stimulation to the patient by a second route, in the form of bright light that is fluctuating in intensity with the vagal stimulation waveform. The bright light waveform may be presented without any delay, or it may be presented after a delay such that the vagal and light waveforms can best entrain one another within the patient's brain. Considering that bright light therapy and vagal nerve stimulation are established treatments for depression, such a novel combined therapy may be most successful for treating depression. However, bright light therapy has also been used successfully to treat PD, and its success with PD patients may be attributable to the regulation of neurotrophic factors in addition to BDNF [Sebastian Paus, Tanja Schmitz-Hubsch, Ullrich Wullner, Antje Vogel, Thomas Klockgether and Michael Abele. Bright Light Therapy in Parkinson's Disease: A Pilot Study. Movement Disorders 22(10, 2007): 1495-1498]. It is understood that other forms of sensory input may also be used in place of, or in addition to, bright light, e.g., audio or tactile input that is presented with the waveform of the vagal nerve stimulator.

To understand how PD symptoms of abnormal movement relate to dopaminergic nerve depletion in the substantia nigra, it is necessary to appreciate how the substantia nigra connects functionally and neuroanatomically to regions of the brain that control movement. Basically, dopaminergic depletion in PD disrupts corticostriatal neuroelectrical balance, leading to increased activity in an indirect circuit and reduced activity in a direct circuit. Those imbalanced corticostriatal connections result in excessive thalamic inhibition, which leads to suppression of the cortical motor system, resulting in akinesia, rigidity, and tremor; and inhibitory descending projection to brain-stem locomotor areas contribute to abnormalities of gait and posture [Lang A E, Lozano A M. Parkinson's disease. Second of two parts. N Engl J Med 339 (No. 16, 1998): 1130-1143; OBESO JA, Rodriguez-Oroz M C, Benitez-Temino B, et al. Functional organization of the basal ganglia: therapeutic implications for Parkinson's disease. Mov. Disord. 23 (Suppl 3, 2008): S548-59]. That understanding provides a rationale for the PD treatments involving deep brain stimulation or ablation that are summarized below.

Currently there is no cure for PD, but therapies are available to treat its symptoms and retard its progression. The drug levodopa (L-DOPA) is the most commonly used treatment. It is transformed into dopamine in dopaminergic neurons and therefore compensates for the lack of dopamine in the substantia nigra. Because L-DOPA may be metabolized before crossing the blood-brain barrier, its meta bolite(s) may cause significant side-effects by virtue of their effects outside the brain. Therefore, peripheral dopa decarboxylase inhibitors (carbidopa and benserazide) are often co-administered with L-DOPA to reduce the side effects. Furthermore, administered L-DOPA inhibits the endogenous formation of dopamine, so its administration eventually becomes counterproductive, such that the PD patient exhibits periods of unresponsiveness to L-DOPA (the so-called "off" periods). At that point, dopamine agonists may be administered, which activate dopamine receptors even in the absence of dopamine. The dopamine agonists include bromocriptine, pergolide, pramipexole, ropinirole, piribedil, cabergoline, apomorphine, and lisuride. In late PD they are useful for reducing the "off" periods. They may also be administered as an initial treatment depending on the age of the patient, before using L-DOPA. In lieu of dopamine agonists, MAO-B inhibitors (selegiline and rasagiline) may also be administered. They increase dopamine levels by inhibiting the rate at which dopamine is degraded.

Excessive muscle contraction in PD occurs when cholinergic function (which increases muscle contraction) is more powerful than dopaminergic function (which decreases muscle contraction). Anti-muscarinics reduce cholinergic function and are therefore sometimes prescribed to bring about more balanced muscular contraction.

Deep brain stimulation (DBS) is currently performed on patients whose PD symptoms cannot be controlled by medication and patients for whom the medications produce unacceptable side effects. DBS is a surgical procedure that electrically stimulates the brain at the sites of implanted electrodes, most often in subthalamic nucleus, the globus pallidus internus, or the ventralis intermedius nucleus of the thalamus. The battery-powered neurostimulator to which the electrodes are attached may be turned off, making DBS effectively reversible, in contrast to irreversible surgical ablation (pallidotomy) at those sites of the brain. Experimental stimulators may also turn themselves off, but stimulate only when the onset of tremors is detected by the device. Use of DBS makes it possible for the PD patients to reduce their medications, thereby also reducing side effects from them. Complications from DBS include those associated with the surgery itself (bleeding, reaction to anesthesia), infection, and cable breakage and migration, as well as problems resulting from the stimulation (e.g., cognitive problems, numbness, double vision, etc. that cannot be corrected by adjusting stimulation parameters) [GARCIA, L., D'Alessandro, G., Bioulac, B., Hammond, C., 2005. High-frequency stimulation in Parkinson's Disease: More or less? Trends Neurosci. 28, 209-216; BITTAR, R. G. Neuromodulation for movement disorders. J. Clin. Neurosci. 13 (2006), 315-318].

Vagal nerve stimulation has been performed on one PD patient who also had epilepsy. When the stimulation intensity was insufficient to control epileptic seizure, the PD symptoms nevertheless improved: resting tremor resolved, bradykinesia improved and the UPDRS score decreased to from 22 to 16. However, the mechanism of that improvement was not addressed. Furthermore, considering that the stimulation parameters were those that had been optimized to treat epilepsy, it is likely that other stimulation parameters may be more suitable for the treatment of PD [S. BOKKALA-PINNINTI, N. Pinninti and S. Jenssen. Vagus nerve stimulation effective for focal motor seizures and focal interictal parkinsonian symptoms—A case report. Journal of Neurology 255(2008, 2): 301-302].

Other forms of non-invasive stimulation are commonly used to treat the motor dysfunction of PD patients—repetetive transcranial magnetic stimulation (rTMS) and electroconvulsive therapy (ECT). These methods stimulate the brain directly rather stimulate the vagus nerve [F FREGNI, D K Simon, A Wu, A Pascual-Leone. Non-invasive brain stimulation for Parkinson's disease: a systematic review and meta-analysis of the literature. J Neurol Neurosurg Psychiatry 2005; 76:1614-1623; LEFAUCHEUR, J. P., Drouot, X., Von Raison, F., Menard-Lefaucheur, I., Cesaro, P., Nguyen, J. P., 2004. Improvement of motor performance and modulation of cortical excitability by repetitive transcranial magnetic stimulation of the motor cortex in Parkinson's Disease. Clin. Neurophysiol. 115, 2530-2541]. Although the reported rTMS protocols for treating PD were generally found to improve motor function, interpretation of their results is complicated by heterogeneity of the patients' medication status, the use of circular versus figure-of-eight stimulation coils, stimulation at different anatomical locations, the use of low-frequency stimulation (from 0.2 to 1 Hz) versus high-frequency stimulation (5, 10 or 20 Hz), the use of subthreshold stimulation versus supra-threshold stimulation, and the use of different methods of assessing benefit. One such protocol demonstrated that improved motor performance in PD after repeated sessions of rTMS may be related to an elevation of serum dopamine concentration [KHEDR, E. M., Rothwell, J. C., Shawky, O. A., Ahmed, M. A., Foly, N., Hamdy, A., 2007. Dopamine levels after repetitive transcranial magnetic stimulation of motor cortex in patients with Parkinson's Disease: preliminary results. Mov. Disord. 2, 1046-1050]. In primates, ECT has also been shown to increase dopaminergic neurotransmission [Anne M LANDAU, M Mallar Chakravarty, Campbell M Clark, Athanasios P Zis and Doris J. Doudet. Electroconvulsive Therapy Alters Dopamine Signaling in the Striatum of Non-human Primates. Neuropsychopharmacology, (13 Oct. 2010, Epub ahead of print)].

The foregoing review of PD disclosed six novel mechanisms by which stimulation of the vagus nerve may be used to treat PD: (1) stimulate the vagus nerve in such a way as to prevent toxins (environmental toxin, virus, or alpha-synuclein clusters) from reaching the dorsal motor nucleus of the vagus nerve, to serve as an antidote to toxins that have already reached that location, and to prevent the pathology from progressing up the neuroaxis; (2) stimulate the vagus nerve in such a way as to enhance the availability or effectiveness of TGF-beta or other anti-inflammatory cytokines; (3) stimulate the vagus nerve in such a way as to enhance the availability or effectiveness of retinoic acid; (4) stimulate the vagus nerve in such a way as to suppress the release or effectiveness of pro-inflammatory cytokines, such as TNF-alpha, through a mechanism that is distinct from the one proposed by TRACEY and colleagues; (5) stimulate the vagus nerve in such a way as to promote the expression of the neurotrophic factors such as GDNF and MANF; and (6) present bright light to the patient in such a way that the light varies in intensity with the same waveform as the vagal nerve stimulation waveform.

Embodiments of the invention in which toxins are prevented from affecting the dorsal motor nucleus of the vagus nerve and other locations along the neuroaxis are like embodiments described below for treating PD at or near the substantia nigra, except that parameters of the stimulation (current, frequency, pulse width, duty cycle, etc.) are chosen in such a way as to preferentially treat the selected neuroanatomical locations Thus, in one embodiment of the invention, the vagus nerve in such a way as to enhance the availability or effectiveness of TGF-beta or other anti-inflammatory cytokines. In a related embodiment of the invention, vagal nerve stimulation promotes release of neuron-synthesized retinoic acid. In another embodiment of the invention, patients may be co-treated with all-trans retinoic acid (ATRA), wherein oral retinoic acid is first administered at a dose of 0.1 to 200 mg/sq. m, typically 20 mg/sq. m. If retinoic acid syndrome or other side effects are not observed in the patient, ATRA is thereafter administered daily until vagal nerve stimulation is performed, typically after one week of ATRA administration and no more than about 45 days of ATRA administration. It is understood that other retinoids, such as 9-cis-retinoic acid and 13-cis-retinoic acid, and any other agent that biases TGF-β towards its anti-inflammatory potential, may be substituted for ATRA, and that if side effects are found, a reduced dose may be administered [ADAMSON, P. C., Bailey, J., Pluda, J., Poplack, D. G. Bauza, S., Murphy, R. F., Yarchoan, R., and Balis, F. M. Pharmacokinetics of all-trans-retinoic acid administered on an intermittent schedule. J. Clin. Oncol., 13: 1238-1241, 1995].

In another embodiment of the invention, the vagus nerve is stimulated in such a way as to promote the expression of the neurotrophic factors such as GDNF and MANF. This may be performed with or without the additional presentation of bright light to the patient in such a way that the light varies in intensity with the same waveform as the vagal nerve stimulation waveform. If co-treatment with light is performed, the luminance is greater than 2500 lux, typically 7500 lux. The light source preferentially produces white or short wavelength light, such as blue light. Furthermore, output of light from the light source follows the supply of energy to the light source, such that when power is supplied or removed, the light rapidly appears or disappears without any significant lag. In the preferred embodiment, the light source comprises light-emitting diodes (LEDs). In another embodiment of the invention, the vagus nerve in such a way as to suppress the release or effectiveness of pro-inflammatory cytokines, such as TNF-alpha, via anti-inflammatory cytokine, retinoic acid and neurotrophic pathways.

In the preferred embodiment of treating PD, the method stimulates the vagus nerve as indicated in FIGS. 6 and 7, using the magnetic stimulation devices that are disclosed herein. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz, typically 20 Hz. The stimulation may be performed for 1 to 200 minutes, typically for 30 minutes. Typically, the treatment is performed repeatedly, e.g., once a month for six months. However, parameters of the stimulation may be varied in order to obtain a beneficial response, as indicated, for example, by the measuring levels and/or activities of anti-inflammatory cytokines, pro-inflammatory cytokines, retinoic acid, and/or neurotrophic factors in the patient's peripheral circulation and/or in the patient's cerebrospinal fluid and/or tissue, before, during or subsequent to each treatment. A beneficial response may also be determined through use of standard diagnosis and treatment evaluation tools for PD, such as the Unified Parkinson's Disease Rating Scale (UPDRS).

Example: Stimulation of the Vagus Nerve to Treat Multiple Sclerosis

Myelin is a dielectric material that forms a natural layer (sheath) around the axon of certain neurons. The presence of a myelin sheath increases the speed at which electrical impulses propagate along those axons, through a process known as saltation. Myelin is composed of about 80% lipid (principally galactocerebroside and sphingomyelin) and about 20% protein (principally myelin basic protein, myelin oligodendrocyte glycoprotein, and proteolipid protein). Myelin is formed and maintained by Schwann cells for axons within the peripheral nervous system and by interfascicular oligodendrocytes for axons within the central nervous system.

Demyelination is the loss of myelin sheaths around axons. It is the primary cause of a category of neurodegenerative autoimmune diseases in which the immune system pathologically damages the nervous system by destroying myelin. These demyelinating diseases include multiple sclerosis, acute disseminated encephalomyelitis, transverse myelitis, chronic inflammatory demyelinating polyneuropathy, Guillain-Barré Syndrome, central pontine myelinosis, leukodystrophy, and Charcot Marie Tooth disease. In what follows, methods of treating multiple sclerosis (MS) are disclosed, but it is understood that the disclosure applies also to other demyelinating neurodegenerative diseases.

MS has no generally accepted formal definition, so that a large number of so-called idiopathic inflammatory demyelinating diseases, also known as borderline forms of MS, may also be treated by the disclosed methods, to the extent that autoimmunity is involved in their pathophysiology (e.g., optic-spinal MS, Devic's disease, acute disseminated encephalomyelitis, Balo concentric sclerosis, Schilder disease, Marburg M S, tumefactive MS, pediatric and pubertal MS, and venous MS). To that same extent, the disclosed methods would also apply to dysmyelination disease, viz., diseases involving the formation of defective myelin without the formation of plaques, including leukodystrophies (Pelizaeus-Merzbacher disease, Canavan disease, phenylketonuria) and schizophrenia.

In MS, nerves of the brain and spinal cord not only become demyelinated, but there is also scarring (formation of scleroses, also known as plaques or lesions) of the nervous tissue, particularly in the white matter of the brain and spinal cord, which is mainly composed of myelin. The neurons in white matter carry signals between grey matter areas of the central nervous system (where information processing is performed) and the rest of the body. In MS, the demyelination is found only rarely in the peripheral nervous system [COMPSTON A and Coles A. Multiple sclerosis. Lancet 372 (9648, October 2008): 1502-1517].

The destruction of myelin takes place concomitantly with destruction of the oligodendrocytes that are responsible for the formation and maintenance of myelin sheaths. As the body's own immune system attacks and damages the myelin, myelin sheaths are damaged or lost, and axons can no longer effectively conduct signals. The inability to conduct nerve signals leads to symptoms that correspond to the particular nervous tissue that has been damaged [Kenneth J. SMITH and W. I. McDonald. The pathophysiology of multiple sclerosis: the mechanisms underlying the production of symptoms and the natural history of the disease. Philos Trans R Soc Lond B Biol Sci. 1999 Oct. 29; 354(1390): 1649-1673].

Because the demyelination can occur essentially anywhere in the white matter of the brain and spinal cord, the MS patient can initially exhibit almost any neurological symptom, making an initial diagnosis of MS difficult. Such symptoms include impairment of the central nervous system (fatigue, depression and moodiness, or cognitive dysfunction), visual problems (inflammation of the optic nerve, double vision, or involuntary eye movement), inability to articulate or swallow, muscle problems (weakness, spasm, or lack of coordination), sensation problems (pain, insensitivity, tingling, prickliness, or numbness), bowel problems (constipation, diarrhea, or incontinence), and urinary problems (incontinence, overactive bladder, or retention). In order of frequency, the most common initial MS symptoms are changes in sensation, vision loss, weakness, double vision, unsteady walking, and imbalance. Fifteen percent of MS patients have multiple initial symptoms.

Following the initial symptoms, a period of months to years of remission may elapse. Thereafter, acute periods of relapse may occur, followed by another remission or a gradual deterioration of neurologic function. New symptoms may also arise during each relapse. Progression of the disease is heterogeneous among MS patients, and subtypes of MS are recognized, based upon the regularity of the acute relapse and subsequent remission, the magnitude of the relapse, and the extent to which progressive deterioration occurs between acute relapses. The most common pattern of MS is known as relapsing-remitting MS (RRMS), in which unpredictable acute relapses may sometimes produce little or no lasting symptoms, followed by periods of no change, followed by another relapse, etc. RRMS usually begins with a clinically isolated syndrome (CIS) attack that only suggests MS, which develops into MS in only 30 to 70 percent of CIS patients.

Standard diagnostic tools for MS are neuroimaging, analysis of cerebrospinal fluid, and evoked potentials. The neuroimaging includes the use of MRI to show plaque location. The analysis of cerebrospinal fluid measures factors that would indicate the presence of chronic inflammation. The evoked potentials comprise neural stimulation that seeks to determine the existence of a reduced neural response that would indicate demyelination.

Many potential triggers of MS acute relapses have been examined, but only a few of them are often acknowledged as being likely triggers, such as the season of the year (spring and summer), viral infection, and stress.

Epidemiological studies have also examined the likelihood that an individual will ever have MS. More than 300 thousand individuals suffer from MS in North America. Worldwide, incidence of MS is significantly higher at locations closer to the north and south poles. Migration studies show that if the exposure to a higher risk environment occurs before the age of 15 years, the migrant assumes the higher risk of the earlier environment. Epidemics of MS have been reported, most notably in the Faroe Islands, but no causative agent has been identified.

The disease onset usually occurs in young adulthood, peaking between the ages of 20 and 30, and it is 1.4 to 3.1 times more common in females than males. Known genetic variations predispose an individual to have MS, with Caucasian populations being at greater risk than Asian or African populations. Although there is a tendency for MS to run in families, only 35% of monozygotic twins both have MS. Some environmental factors also increase the risk of MS, such as decreased exposure to sunlight and infection with the Epstein-Barr virus at a young age. However, there is no set of risk factors that can reliably predict the onset of MS.

It is generally recognized that MS is an autoimmune disease in which T cells of the immune system gain entrance to the brain when the blood-brain barrier (BBB) is compromised, leading to inflammation in the brain and spinal cord. A deficiency in uric acid is implicated in compromise of the BBB, and individuals with elevated uric acid (e.g., gout patients) are at decreased risk of developing MS. The T cells recognize myelin as foreign and attack it, triggering inflammatory processes and stimulating other immune cells and soluble factors such as cytokines and antibodies. Myelinating oligodendrocytes (either mature or derived from stem cells) can repair some of the demyelination, but if the inflammation is prolonged or frequent, the damage eventually becomes unrepairable, and a scarring (sclerosis) accumulates around the demyelinated neurons. Furthermore, the axons of the corresponding neurons may also be damaged, probably by B-Cells of the immune system.

There is no known cure for MS. The current therapeutic practice is to relieve symptoms during and between acute attacks and to attempt to reduce the likelihood of relapses, thereby slowing progression of the disease. Symptomatic treatment involves administration of corticosteroids, such as methylprednisolone, to reduce inflammation during attacks. Other drugs are used to treat the symptoms of spasticity (baclofen, tizanidine, diazepam, clonazepam, dantrolene), optic neuritis (methylprednisolone and oral steroids), fatigue (amantadine, pemoline), pain (codeine), trigeminal neuralgia (carbamazepine), and sexual dysfunction (papaverine for men).

To prevent relapses, the following drugs are currently used: Interferon beta-1a, interferon beta-1b, glatiramer acetate, mitoxantrone, and natalizumab. These interferons are anti-viral proteins that may suppress the immune system. Mitoxantrone is also an immunosuppressant that suppresses the proliferation of T cells and B cells. Natalizumab is a monoclonal antibody that blocks the ability of inflammatory immune cells to attach to and pass through the cell layers lining the blood-brain barrier, by binding to the cellular adhesion molecule a4-integrin. Glatiramer acetate is an immunomodulator drug that shifts the population of T cells from pro-inflammatory Th1 cells to regulatory Th2 cells, by virtue of its resemblance to myelin basic protein. Each of these drugs produces significant side effects. For example, glatiramer acetate and the interferon treatments produce irritation at the injection site. Interferons also produce flu-like symptoms and may cause liver damage. Mitoxantrone may cause cardiotoxicity. Natalizumab may cause multifocal leukoencephalopathy.

Experimental treatments for MS include plasma exchange, bone marrow transplantation, potassium channel blockers to improve the conduction of nerve impulses, the inducement of an immune attack against myelin-destroying T cells (vaccination and peptide therapy), protein antigen feeding to release the protective cytokine TGF-beta, administration of TGF-beta, use of monoclonal antibodies to promote remyelination, and various dietary therapies. Many such experimental treatments are motivated by experiments using an animal model of brain inflammation diseases including MS, namely, experimental allergic encephalomyelitis (EAE) [HAFLER D A, Kent S C, Pietrusewicz M J, Khoury S J, Weiner H L and Fukaura H. Oral administration of myelin induces antigen-specific TGF-beta 1 secreting T cells in patients with multiple sclerosis. Ann N Y Acad Sci 1997; 56:120-131; MIRSHAFIEY A, Mohsenzadegan M. TGF-beta as a promising option in the treatment of multiple sclerosis. Neuropharmacology 56(6-7, 2009):929-36].

To date, electrical stimulation therapies have stimulated nerves of MS patients other than the vagus nerve, primarily to treat symptoms such as urinary incontinence and spasticity [KRAUSE P, Szecsi J, Straube A. FES cycling reduces spastic muscle tone in a patient with multiple sclerosis. NeuroRehabilitation. 2007; 22(4):335-7]; P. KETELAER, G. Swartenbroekx, P. Deltenre, H. Carton and J. Gybels. Percutaneous epidural dorsal cord stimulation in multiple sclerosis. Acta Neurochirurgica 49 (1979): 95-101; L. S. ILLIS and E. M. Sedgwick. Dorsal column stimulation in multiple sclerosis. Br Med J. (1980 Aug. 16); 281(6238): 518]. Electrical stimulation of the vagus nerve of MS patients has been reported in connection with treatment of tremor and dysphagia [F. MARROSU, A. Maleci, E. Cocco, M. Puligheddu, and M. G. Marrosu. Vagal nerve stimulation effects on cerebellar tremor in multiple sclerosis. Neurology 65 (2005): 490; F MARROSU, A Maleci, E Cocco, M Puligheddu, L Barberini and M G Marrosu. Vagal nerve stimulation improves cerebellar tremor and dysphagia in multiple sclerosis. Multiple Sclerosis 2007; 13: 1200-1202].

Patent application US20040249416, entitled Treatment of conditions through electrical modulation of the autonomic nervous system, to YUN et al. mentions treatment of multiple sclerosis within a long list of diseases, in connection with stimulation of the vagus and other nerves. However, it makes no mention of modulating the activity of cytokines or neurotrophic factors.

U.S. Pat. No. 6,610,713 and U.S. Pat. No. 6,838,471, entitled Inhibition of inflammatory cytokine production by cholinergic agonists and vagus nerve stimulation, to TRACEY, mention treatment of multiple sclerosis within a long list of diseases, in connection with the treatment of inflammation through stimulation of the vagus nerve. According to those patents, "Inflammation and other deleterious conditions . . . are often induced by proinflammatory cytokines, such as tumor necrosis factor (TNF; also known as TNF.alpha. or cachectin) . . . " The patents goes on to state that "Proinflammatory cytokines are to be distinguished from anti-inflammatory cytokines, . . . , which are not mediators of inflammation." It is clear from those patents that their objective is only to suppress the release of proinflammatory cytokines, such as TNF-alpha. There is no mention or suggestion that the method is intended to stimulate the release of anti-inflammatory cytokines, and in fact the text quoted above disclaims a role for anti-inflammatory cytokines as mediators of inflammation. Those patents make a generally unjustified dichotomy between pro- and anti-inflammatory cytokines, by indicating that a cytokine could be one or the other but not both. In particular, the patents make no mention of the cytokine TGF-beta, and there is no suggestion that the role of a cytokine in regards to its pro- or anti-inflammation competence may be inherently indeterminate or indefinite unless more information is provided about the presumed physiological environment in which the cytokine finds itself.

Treatment of multiple sclerosis is also mentioned within long lists of diseases in the following related applications to TRACEY and his colleague HUSTON, wherein stimulation of the vagus nerve is intended to suppress the release of proinflammatory cytokines such as TNF-alpha: US20060178703, entitled Treating inflammatory disorders by electrical vagus nerve stimulation, to HUSTON et al.; US20050125044, entitled Inhibition of inflammatory cytokine production by cholinergic agonists and vagus nerve stimulation, to TRACEY; US20080249439, entitled Treatment of inflammation by non-invasive stimulation to TRACEY et al.; US20090143831, entitled Treating inflammatory disorders by stimulation of the cholinergic anti-inflammatory pathway, to HUSTON et al; US 20090248097, entitled Inhibition of inflammatory cytokine production by cholinergic agonists and vagus nerve stimulation, to TRACEY et al. The same observations made above in connection with U.S. Pat. No. 6,610,713 and U.S. Pat. No. 6,838,471 apply to those applications as well.

The present invention discloses methods for using vagal nerve stimulation to suppress inflammation. However, unlike the patents and applications to TRACEY and to HUSTON, the present invention discloses use of vagal nerve stimulation to increase the concentration or effectiveness of anti-inflammatory cytokines. TRACEY et al do not consider the modulation of anti-inflammatory cytokines to be part of the cholinergic anti-inflammatory pathway that their method of vagal nerve stimulation is intended to activate. Thus, they explain that "activation of vagus nerve cholinergic signaling inhibits TNF (tumor necrosis factor) and other proinflammatory cytokine overproduction through 'immune' a7 nicotinic receptor-mediated mechanisms" [V. A. PAVLOV and K. J. Tracey. Controlling inflammation: the cholinergic anti-inflammatory pathway. Biochemical Society Transactions 34, (2006, 6): 1037-1040]. In contrast, anti-inflammatory cytokines are said to be part of a different "diffusible anti-inflammatory network, which includes glucocorticoids, anti-inflammatory cytokines, and other humoral mediators" [CZURA C J, Tracey K J. Autonomic neural regulation of immunity. J Intern Med. 257(2005, 2): 156-66]. Their disclaiming of a role for anti-inflammatory cytokines as mediators of inflammation following stimulation of the vagus nerve may be due to a recognition that anti-inflammatory cytokines (e.g. TGF-β) are produced constitutively while pro-inflammatory cytokines (e.g., TNF-alpha) are not, but are instead induced. However, anti-inflammatory cytokines are inducible as well as constitutive, so that for example, an increase in the concentrations of potentially anti-inflammatory cytokines such as transforming growth factor-beta (TGF-β) can in fact be accomplished through stimulation of the vagus nerve [R A BAUMGARTNER, V A Deramo and M A Beaven. Constitutive and inducible mechanisms for synthesis and release of cytokines in immune cell lines. The Journal of Immunology 157 (1996, 9): 4087-4093; CORCORAN, Ciaran; Connor, Thomas J; O'Keane, Veronica; Garland, Malcolm R. The effects of vagus nerve stimulation on pro- and anti-inflammatory cytokines in humans: a preliminary report. Neuroimmunomodulation 12 (5, 2005): 307-309].

In MS, the strategy of inhibiting pro-inflammatory cytokines rather than enhancing anti-inflammatory cytokines might even be counterproductive. Thus, blocking TNF-alpha with the drug Ienercept promotes and exacerbates MS attacks rather than delaying them, which might be attributable in part to the fact that TNF-alpha promotes remyelination and the proliferation of oligodendrocytes that perform the myelination. [ANONYMOUS. TNF neutralization in MS: Results of a randomized, placebo controlled multicenter study. Neurology 1999, 53:457; ARNETT H A, Mason J, Marino M, Suzuki K, Matsushima G K, Ting J P. TNF alpha promotes proliferation of oligodendrocyte progenitors and remyelination. Nat Neurosci 2001, 4:1116-1122].

TGF-β is currently used as an experimental treatment for multiple sclerosis [MIRSHAFIEY A, Mohsenzadegan M. TGF-beta as a promising option in the treatment of multiple sclerosis. Neuropharmacology. 56 (2009, 6-7): 929-36]. In the method disclosed herein, it is applied directly as a drug, indirectly through stimulation of the vagus nerve without pharmacological administration to the patient, or both directly and indirectly.

TGF-β converts undifferentiated T cells into regulatory T (Treg) cells that block autoimmunity. However, in the presence of interleukin-6, TGF-β also causes the differentiation of T lymphocytes into proinflammatory IL-17 cytokine-producing T helper 17 (TH17) cells, which promote autoimmunity and inflammation. Thus, it is conceivable that an increase of TGF-β levels might actually cause or exacerbate inflammation, rather than suppress it. Accordingly, a step in the method that is disclosed here is to deter TGF-β from realizing its pro-inflammatory potential, by selecting electrical stimulation parameters that bias the potential of TGF-β towards anti-inflammation, and/or by treating the patient with an agent such as the vitamin A metabolite retinoic acid that is known to promote such an anti-inflammatory bias [MUCIDA D, Park Y, Kim G, Turovskaya O, Scott I, Kronenberg M, Cheroutre H. Reciprocal TH17 and regulatory T cell differentiation mediated by retinoic acid. Science 317(2007, 5835): 256-60; Sheng XIAO, Hulin Jin, Thomas Korn, Sue M. Liu, Mohamed Oukka, Bing Lim, and Vijay K. Kuchroo. Retinoic acid increases Foxp3+ regulatory T cells and inhibits development of Th17 cells by enhancing TGF-β-driven Smad3 signaling and inhibiting IL-6 and IL-23 receptor expression. J. Immunol. 181(2008, 4): 2277-2284].

In one embodiment of the invention, endogenous retinoic acid that is produced and released by neurons themselves is used to produce the anti-inflammatory bias. Thus, it is known that vagal nerve stimulation may induce differentiation through release of retinoic acid that is produced in neurons from retinaldehyde by retinaldehyde dehydrogenases, and the disclosed invention claims to induce anti-inflammatory regulatory T cell (Treg) differentiation by this type of mechanism [van de PAVERT S A, Olivier B J, Goverse G, Vondenhoff M F, Greuter M, Beke P, Kusser K, Höpken U E, Lipp M, Niederreither K, Blomhoff R, Sitnik K, Agace W W, Randall T D, de Jonge W J, Mebius R E. Chemokine CXCL13 is essential for lymph node initiation and is induced by retinoic acid and neuronal stimulation. Nat Immunol. 2009 November; 10(11):1193-9]. It is understood that the methods that are disclosed here in connection with the treatment of MS may be applied to the treatment of other diseases that involve inflammation, such as post-operative ileus.

Thus, the present invention comprises a pro-anti-inflammatory mechanism because it biases the competence of TGF-beta towards that of an anti-inflammatory cytokine. An increase in the concentrations of potentially anti-inflammatory cytokines such as TGF-β can also be accomplished through stimulation of the vagus nerve, which is also a pro-anti-inflammatory mechanism when TGF-β is biases towards anti-inflammation [CORCORAN, Ciaran; Connor, Thomas J; O'Keane, Veronica; Garland, Malcolm R. The effects of vagus nerve stimulation on pro- and anti-inflammatory cytokines in humans: a preliminary report. Neuroimmunomodulation 12 (5, 2005): 307-309]. As mentioned above, inhibiting the pro-inflammatory cytokine TNF-alpha is considered to be counterproductive in MS patients, there may be circumstances in which the inhibition of other pro-inflammatory cytokines may be useful therapeutically. In that case, stimulation of the vagus nerve in an attempt to produce the anti-pro-inflammatory response advocated by TRACEY and colleagues may be attempted. However, an anti-pro-inflammatory response may be produced by another mechanism involving stimulation of the vagus nerve, because as indicated above, vagal nerve stimulation may result in the release of retinoic acid, and the retinoic acid itself inhibits pro-inflammatory cytokines [Malcolm Maden. Retinoic acid in the development, regeneration and maintenance of the nervous system. Nature Reviews Neuroscience 8 (2007), 755-765].

The potentially anti-inflammatory cytokine TGF-beta is a member of the TGF-beta superfamily of neurotrophic factors. Neurotrophic factors serve as growth factors for the development, maintenance, repair, and survival of specific neuronal populations, acting via retrograde signaling from target neurons by paracrine and autocrine mechanisms. Other neurotrophic factors also promote the survival of neurons during neurodegeneration. These include members of the nerve growth factor (NGF) superfamily, the glial-cell-line-derived neurotrophic factor (GDNF) family, the neurokine superfamily, and non-neuronal growth factors such as the insulin-like growth factors (IGF) family. However, major problems in using such neurotrophic factors for therapy are their inability to cross the blood-brain-barrier, adverse effects resulting from binding to the receptor in other organs of the body and their low diffusion rate [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127].

It is known that vagal nerve stimulation and transcranial magnetic stimulation can increase the levels of at least one neurotrophic factor in the brain, brain-derived neurotrophic factor (BDNF), which has been studied extensively in connection with the treatment of depression [Follesa P, Biggio F, Gorini G, Caria S, Talani G, Dazzi L, Puligheddu M, Marrosu F, Biggio G. Vagus nerve stimulation increases norepinephrine concentration and the gene expression of BDNF and bFGF in the rat brain. Brain Research 1179 (2007): 28-34; Biggio F, Gorini G, Utzeri C, 011a P, Marrosu F, Mocchetti I, Follesa P. Chronic vagus nerve stimulation induces neuronal plasticity in the rat hippocampus. Int J Neuropsychopharmacol. 12(9, 2009):1209-21; Roberta Zanardini, Anna Gazzoli, Mariacarla Ventriglia, Jorge Perez, Stefano Bignotti, Paolo Maria Rossini, Massimo Gennarelli, Luisella Bocchio-Chiavetto. Effect of repetitive transcranial magnetic stimulation on serum brain derived neurotrophic factor in drug resistant depressed patients. Journal of Affective Disorders 91 (2006) 83-86]. It has never been proposed before the present disclosure that vagal nerve stimulation may be utilized to increase BDNF levels in MS patients. BDNF is known to reduce clinical inflammation and cell death in an animal model of MS [Makar T K, Trisler D, Sura K T, Sultana S, Patel N, Bever C T. Brain derived neurotrophic factor treatment reduces inflammation and apoptosis in experimental allergic encephalomyelitis. J Neurol Sci. 270(1-2, 2008):70-6]. Vagal nerve stimulation may likewise promote the expression of other beneficial neurotrophic factors as well, which circumvents the problem of blood-brain barrier blockage by being induced through vagal nerve stimulation. Patent application US20100280562, entitled Biomarkers for monitoring treatment of neuropsychiatric diseases, to PI et al, disclosed the measurement of BDNF following vagal nerve stimulation. However, that application is concerned with the search for biomarkers involving the levels of BDNF, rather than a method for treating a neurodegenerative disease using vagal nerve stimulation.

The foregoing review of MS disclosed four novel mechanisms by which stimulation of the vagus nerve may be used to treat MS: (1) stimulate the vagus nerve in such a way as to enhance the availability or effectiveness of TGF-beta or other anti-inflammatory cytokines; (2) stimulate the vagus nerve in such a way as to enhance the availability or effectiveness of retinoic acid; (3) stimulate the vagus nerve in such a way as to suppress the release or effectiveness of pro-inflammatory cytokines, through a mechanism that is distinct from the one proposed by TRACEY and colleagues; (4) stimulate the vagus nerve in such a way as to promote the expression of the neurotrophic factors such as BDNF.

In one embodiment of the invention, patients may be co-treated with all-trans retinoic acid (ATRA), wherein oral retinoic acid is first administered at a dose of 0.1 to 200 mg/sq. m, typically 20 mg/sq. m. If retinoic acid syndrome or other side effects are not observed in the patient, ATRA is thereafter administered daily until vagal nerve stimulation is performed, typically after one week of ATRA administration and no more than about 45 days of ATRA administration. It is understood that other retinoids, such as 9-cis-retinoic acid and 13-cis-retinoic acid, and any other agent that biases TGF-$\beta$ towards its anti-inflammatory potential, may be substituted for ATRA, and that if side effects are found, a reduced dose may be administered [ADAMSON, P. C., Bailey, J., Pluda, J., Poplack, D. G. Bauza, S., Murphy, R. F., Yarchoan, R., and Balis, F. M. Pharmacokinetics of all-trans-retinoic acid administered on an intermittent schedule. J. Clin. Oncol., 13: 1238-1241, 1995].

In another embodiment of the invention, vagal nerve stimulation itself promotes release of neuron-synthesized retinoic acid, thereby inducing the differentiation undifferentiated T cells into anti-inflammatory regulatory T cells (Treg) in the presence of the cytokine TGF-beta. In yet another embodiment of the invention, both endogenous (induced by vagal nerve stimulation) and exogenous retinoic acid (administered as a drug) are used to induce differentiation of undifferentiated T cells into regulatory T (Treg) cells. Other aspects of the invention are that TGF-beta itself may be induced by the vagal nerve stimulation, the release of proinflammatory cytokines such as TNF-alpha may be blocked by the vagal nerve stimulation, and neurotrophic factors such as BDNF may be induced by the vagal nerve stimulation.

In the preferred embodiment of treating MS, the method stimulates the vagus nerve as indicated in FIGS. 6 and 7, using the magnetic stimulation devices that are disclosed herein. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz, typically 20 Hz. The stimulation may be performed for 1 to 200 minutes, typically for 30 minutes. Typically, the treatment is performed repeatedly, e.g., once a month for six months or throughout a period of remission. However, parameters of the stimulation may be varied in order to obtain a beneficial response, as indicated, for example, by measuring levels and/or activities of TGF-$\beta$ or other anti-inflammatory cytokines, pro-inflammatory cytokines, and/or neurotrophic factors such as BDNF in the patient's peripheral circulation and/or in the patient's cerebrospinal fluid, before, during and subsequent to each treatment. A beneficial response may also be determined through use of standard diagnostic tools for MS, including neuroimaging, analysis of cerebrospinal fluid, and evoked potentials. The treatment is primarily intended to prevent MS relapses during remission, but it may also be administered to patients while a MS relapse is in progress, so as to hasten entry into remission.

Example: Stimulation of the Vagus Nerve to Treat Postoperative Cognitive Dysfunction and/or Postoperative Delirium Postoperative cognitive dysfunction (POCD) is a loss in cognitive function after surgery. The loss may include memory, the ability to learn, the ability to concentrate, and/or the ability to reason and comprehend. The cognitive decline may be subtle, such that psychological testing is needed to detect it, or it may be profound and obvious.

POCD does not refer to delirium that may occur immediately after surgery, but instead refers to cognitive loss that may persist weeks, months, or permanently after the surgery. However, postoperative cognitive dysfunction and postoperative delirium (POD) are not mutually exclusive. They may in fact have risk factors, mechanisms, and treatment options in common. Accordingly, background information pertaining to POD is presented below, after first discussing POCD and disclosing methods for treating POCD.

A limited number of studies have been conducted to evaluate whether certain demographic populations are at higher risk to suffer from POCD, whether the risk is contingent on the type of surgery, whether the risk depends on the anesthesia that was used, how the medical condition of the patient prior to the surgery influences the risk, whether drug sensitivity is involved, and whether these variables influence the duration of the POCD, its preventability, or its treatability. Elderly patients are at greatest risk for developing POCD. A low level of education predisposes a risk of POCD. Patients undergoing cardiac surgery are at greatest risk, especially those with progressive atherosclerosis. However, major surgery in general poses a greater risk of developing POCD than minor surgery. The incidence of prolonged POCD is apparently similar regardless of the anesthetic technique used, suggesting that nonanesthetic factors are likely to be important. However, use of regional anesthesia decreases the incidence of POCD early after surgery. [Lars S. RASMUSSEN. Postoperative cognitive dysfunction: Incidence and prevention. Best Practice & Research Clinical Anesthesiology 20(2006, No. 2): 315-330; Ola A. SELNES and Guy M. McKhann. Neurocognitive Complications after Coronary Artery Bypass Surgery. Ann Neurol 2005; 57:615-621; Ramesh RAMAIAH and Arthur M. Lam. Postoperative Cognitive Dysfunction in the Elderly. Anesthesiology Clin 27 (2009): 485-496; Anne-Mette SAUËR, Cornelis Kalkman and Diederik van Dijk. Postoperative cognitive decline. J Anesth (2009) 23:256-259].

The pathophysiology of POCD has been investigated in view of the above clinical findings and in the context of cellular responses to surgery in general [Niamh Ni CHOILEAIN and H. Paul Redmond. Cell response to surgery. Arch Surg 2006; 141:1132-40; XIE GL, Zhang W, Chang Y Z, Chu Q J. Relationship between perioperative inflammatory response and postoperative cognitive dysfunction in the elderly. Med Hypotheses 2009; 73:402-3; HU Z, Ou Y, Duan K, Jiang X. Inflammation: a bridge between postoperative cognitive dysfunction and Alzheimer's disease. Med Hypotheses. 2010 April; 74(4):722-4].

Although the cause of POCD appears to be multifactorial, the response of the body to the surgery itself appears to be a primary contributing factor. This is because decreased surgical trauma is associated with a decreased risk of POCD, and the stress of surgery triggers an inflammatory response with release of cytokines that may be responsible for changes in brain function and recovery. Furthermore, a correlation has been observed in patients' interleukin-6, cortisol and late functional recovery. Animal experiments also indicate that there is a relation between cytokine-mediated inflammation and POCD [Y WAN, J Xu, D Ma, Y Zeng, M Cibelli, M Maze. Postoperative impairment of cognitive function in rats: a possible role for cytokine-mediated inflammation in the hippocampus. Anesthesiology 2007; 106:436-43].

There is currently no generally agreed-upon treatment for POCD. Primary prevention by providing good oxygenation and cerebral perfusion during surgery, and adequate analgesia and emotional support after surgery have been suggested, including the use of occupational therapy and biofeedback. Medical conditions that could also contribute to POCD should also be treated, such as hypothyroidism. Otherwise, there are few treatment options. XIONG et al suggested that transcutaneous stimulation of the vagus nerve may attenuate the inflammatory response that appears to be associated with POCD. Their suggestion was that the stimulation be transcutaneous because implantation of a vagal nerve stimulator by surgery may exacerbate the very surgery-induced problem that the stimulation is intended to treat. [XIONG J, Xue F S, Liu J H, Xu Y C, Liao X, Zhang Y M, Wang W L, Li S. Transcutaneous vagus nerve stimulation may attenuate postoperative cognitive dysfunction in elderly patients. Medical Hypotheses 73 (2009) 938-941].

However, the site of transcutaneous vagal stimulation that XIONG et al suggest is the external auditory canal. This may not be as effective as stimulating at the site where vagus nerve stimulators are ordinarily implanted, namely, in the neck. Furthermore, XIONG et al do not suggest stimulation parameters that should be used. Accordingly, methods are disclosed here to better treat POCD patients. The methods counteract inflammation by any of the mechanisms shown in FIG. 8.

In the preferred embodiment, the method stimulates the vagus nerve in the neck as indicated in FIGS. 6 and 7, using the magnetic stimulation devices that are disclosed herein. The position is adjusted about that location, and the angular orientation of the device is also rotated about that location, until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed repeatedly, e.g., once a week for six months. However, parameters of the stimulation may be varied in order to obtain a beneficial response, as indicated, for example, by the measurement of levels and/or activities of TGF-beta, neurotrophic factors, retinoic acid, and/or TNF-alpha in the patient's peripheral circulation and/or in the patient's cerebrospinal fluid, during and subsequent to each treatment, or by psychological evaluation of the extent of the patient's cognitive dysfunction.

If a patient experiences postoperative delirium before experiencing POCD, the disclosed method of treatment is initially somewhat different, as now described. According to the American Psychiatric Association diagnostic manual (DSM-IV-TR), delirium is a potentially reversible state of acute brain failure with disturbance of consciousness accompanied by cognitive deficits that cannot be accounted for by past or evolving dementia and is associated with evidence of physiological disturbance owing to a medical condition. It is characterized by the inability to focus attention, disorientation that is not attributable to dementia, sleep disturbance, and sometimes disruptive behavior. However, in the elderly, the earliest signs of delirium may be withdrawal rather than agitation.

Postoperative delirium (POD) is delirium that develops acutely after surgery, usually within hours to days, and its severity often fluctuates during the course of the day. The physiological disturbance with which the delirium is associated is the surgery itself. The time-course of POD is typically a shock phase of several hours after surgery in which the patient is hypometabolic, followed by a hypermetabolic inflammatory phase that ordinarily peaks two days after surgery, followed by a return to normal within a week. If the problem does not resolve itself completely within this time frame, the patient may be considered to suffer from postoperative cognitive dysfunction (POCD) rather than POD.

POD occurs in 10 to 50% of postoperative patients and in 80% of elderly patients who require intensive care. Patients undergoing cardiovascular, major abdominal and orthopedic surgery are most prone to develop POD. Twenty five percent of elderly patients who exhibit POD die within six months.

Factors that may predispose to the development of POD include exposure to toxins (including CNS-active drugs and alcohol abuse), infection, inflammation (resulting, for example, from autoimmune disease), trauma including postoperative trauma, decreased cardiac output and/or oxygen saturation, vascular disease, metabolic derangement, vitamin deficiency, central nervous system states such as epilepsy, hydrocephalus, and central nervous system lesions. Prevention or treatment of POD will initially involve the identification, management and/or elimination of such predisposing factors [Yu-Ling CHANG, Yun-Fang Tsai, Pyng-Jing Lin, Min-Chi Chen, and Chia-Yih Liu. Prevalence and risk factors for postoperative delirium in a cardiovascular intensive care unit. American Journal of Critical Care. 2008; 17:567-575; RUDRA A, Chatterjee S, Kirtania J, Sengupta S, Moitra G, Sirohia S, Wankhade R, Banerjee S. Postoperative delirium. Indian J Crit Care Med 2006; 10:235-40].

Behavior suggestive of delirium includes the inability to focus attention, incoherent speech, hallucination, withdrawal or hypervigilance. In contrast to dementia, such behavior with POD may fluctuate significantly over the course of even a few hours. The Delirium Symptom Interview, the Confusion Assessment Method, the Delirium Scale, the Delirium Rating Scale and the Memorial Delirium Assessment Scale are formal psychological measurements that are useful for forming an initial diagnosis of patients who are not agitated.

The antidopaminergic drug haloperidol is often administered intravenously to counter the neuronal dysfunction associated with delirium, especially when agitation is present. This is because psychotic fear in delirium may originate in the amygdala, which abnormally excites dopamine subpopulations that project to limbic areas and to cognitive regions of the cortex and striatum. Thus, fear in delirium requires the use of dopamine-blocking neuroleptics rather than benzodiazepines. However, careful monitoring of the cardiovascular system is necessary because of the potential for ventricular arrhythmia following use of haloperidol [Gregory L. FRICCHIONE, Shamim H. Nejad, Justin A. Esses, Thomas J. Cummings, Jr., John Querques, Ned H. Cassem, and George B. Murray. Postoperative Delirium. Am J Psychiatry 165 (7, July 2008): 803-812].

POD is thought to arise initially because leukocytes adhere to surgically damaged endothelial cells and become activated. Their degranulation releases free oxygen radicals and enzymes, which in turn leads to endothelial cell membrane destruction, loosening of intercellular tights, extravascular fluid shift, and formation of perivascular edema. The immune response in the brain is amplified in patients whose predisposing factors cause the blood-brain barrier to have compromised integrity [James L. RUDOLPH, Basel Ramlawi, George A. Kuchel, Janet E. McElhaney, Dongxu Xie, Frank W. Sellke, Kamal Khabbaz, Sue E. Levkoff, and Edward R. Marcantonio. Chemokines are Associated with Delirium after Cardiac Surgery. J Gerontol A Biol Sci Med Sci. 2008 February; 63(2): 184-189]. The edema in turn produces longer diffusion distance for oxygen to reach nerve cells. Furthermore, the blood flow in individual capillaries may become disrupted. Synthesis and release of the neurotransmitter acetylcholine (ACH) is particularly sensitive to the resulting hypoxia, especially in the elderly.

Such oxidative stress may produce localized neuronal dysfunction in the hippocampus and amygdala, which subsequently progresses to dysfunction in the brainstem, gray matter, and cerebellum. The neuronal dysfunction is associated with neurotransmitter disequilibrium corresponding to decreased acetylcholine and GABA, as well as increased dopamine and glutamate. That neurotransmitter dysfunction ultimately produces the symptoms of delirium. Thus, the decreased ACH leads to a relative excess of dopaminergic transmission, wherein the amygdala projects to dopamine subpopulations in limbic and cognitive areas of the brain that produce fear in delirious patients. [Martin Hala. Pathophysiology of postoperative delirium: Systemic inflammation as a response to surgical trauma causes diffuse microcirculatory impairment. Medical Hypotheses (2007) 68, 194-196]. Accordingly, applicants disclose herein a method for preventing or minimizing excessive development of the perioperative inflammation that leads to POD. The method is like that used to treat POCD in that involves stimulation of the vagus nerve in the neck to increase reserve levels of the neurotransmitter acetylcholine, in such a way as to promote a normal balance of neurotransmitter levels. However, the method differs from that used to treat POCD in that the parameters of the stimulation are selected to specifically promote normal neurotransmitter levels in the amygdala and in the limbic and cognitive areas of the brain to which the amygdala projects. Vagal afferents traverse the brainstem in the solitary tract, with terminating synapses particularly located in the nucleus of the tractus solitarius (NTS). The NTS projects to a wide variety of structures including the para brachial nucleus, which in turn projects to the hypothalamus, the thalamus, the amygdala, the anterior insular, and infralimbic cortex, lateral prefrontal cortex, and other cortical regions. Through its projection to the amygdala, the NTS gains access to amygdala-hippocampus-entorhinal cortex pathways of the limbic system. Thus, the disclosed treatment of POD by vagal nerve stimulation uses parameters (intensity, pulse-width, frequency, duty cycle, etc.) that preferentially activate the limbic system via the amygdala [Jeong-Ho CHAE, Ziad Nahas, Mikhail Lomarev, Stewart Denslow, Jeffrey P. Lorberbaum, Daryl E. Bohning, Mark S. George. A review of functional neuroimaging studies of vagus nerve stimulation (VNS). Journal of Psychiatric Research 37 (2003) 443-455] or by other routes [G. C. Albert, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042 1060].

In the preferred embodiment, the method stimulates the vagus nerve in the neck as indicated in FIGS. 6 and 7, using the magnetic stimulation devices that are disclosed herein. Any of the anti-inflammatory mechanisms shown in FIG. 8 may be induced by the stimulation.

The position of the device is adjusted and the angular orientation of the device is also rotated about an initial location, until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed repeatedly, e.g., before surgery, and daily after surgery. However, parameters of the stimulation may be varied in order to obtain a beneficial response, as indicated, for example, by the measurement of levels and/or activities of TGF-beta, neurotrophic factors, retinoic acid, and/or TNF-alpha in the patient's peripheral circulation and/or in the patient's cerebrospinal fluid, during and subsequent to each treatment, or by psychological evaluation of the extent of the patient's delirium.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a neurodegenerative disorder in a patient, the method comprising:
    positioning a contact surface of a housing in contact with an outer skin surface of a neck of the patient, wherein the housing comprises an energy source configured to generate an electric current;
    transmitting, via the contact surface, the electric current transcutaneously and non-invasively through the outer skin surface of the neck of the patient to generate an electrical impulse at or near a selected nerve within the patient; and
    modulating the electric current such that the electrical impulse comprises bursts of pulses with each of the bursts comprising a frequency from about 5 Hz to about 100 Hz and with each of the pulses comprising a duration from about 50 microseconds to about 1000 microseconds and such that the electrical impulse is sufficient to increase an activity of an anti-inflammatory cytokine in the patient to inhibit an inflammation and thereby treat the neurodegenerative disorder.

2. The method of claim 1, wherein the electrical impulse is sufficient to stimulate a nerve fiber that controls or mediates an activity of a neurotrophic factor.

3. The method of claim 2, wherein the neurotrophic factor is a member of a transforming growth factor (TGF) beta superfamily of neurotrophic factors.

4. The method of claim 2, wherein the neurotrophic factor is a member of at least one of a nerve growth factor superfamily, a neurokine superfamily, or an insulin-like family of non-neuronal growth factors.

5. The method of claim 2, wherein the neurotrophic factor is a member of a same family as at least one of a nerve growth factor (NGF), a glial-cell-line-derived neurotrophic factor (GDNF), a brain-derived neurotrophic factor (BDNF), or a mesencephalic astrocyte-derived neurotrophic factor (MANF).

6. The method of claim 1, wherein the neurodegenerative disorder is selected from a group comprising at least one of Alzheimer's disease, Parkinson's disease, multiple sclerosis, postoperative cognitive dysfunction, or postoperative delirium.

7. The method of claim 1 wherein the selected nerve is a vagus nerve.

8. The method of claim 7 wherein the selected nerve is a right branch of the vagus nerve.

9. The method of claim 1, wherein the electrical impulse is sufficient to inhibit a release of a pro-inflammatory cytokine.

10. The method of claim 9 wherein the pro-inflammatory cytokine is tumor necrosis factor (TNF)-alpha.

11. The method of claim 1 wherein the selected nerve is at least approximately 1-2 cm below an outer skin surface of the patient.

12. The method of claim 1, wherein the electric current is modulated such that the patient has decreased measurable pain.

13. The method of claim 1, wherein the bursts comprise the pulses and at least one of the bursts corresponds to at least one of an up-cycle or a down-cycle of the electrical impulse.

14. An apparatus for applying an electric current to a target region within a patient with a neurodegenerative disorder, the apparatus comprising:
    an enclosure having a contact surface; and
    a power source housed within the enclosure and configured to generate the electric current that is sufficient to transmit an electrical impulse transcutaneously and non-invasively through an outer skin surface of a neck of the patient to a location at or near the target region when the contact surface is positioned against the outer skin surface of the neck of the patient, wherein the electrical impulse comprises bursts of pulses with each of the bursts comprising a frequency from about 5 Hz to about 100 Hz and with each of the pulses comprising a duration from about 50 microseconds to about 1000 microseconds and such that the electrical impulse is sufficient to modulate an activity of a selected nerve at or near the target region to increase an activity of an anti-inflammatory cytokine in the patient and thereby treat the neurodegenerative disorder.

15. The apparatus of claim 14, further comprising:
    a conduction medium contained within the enclosure, wherein the electrical impulse passes through the conduction medium, the contact surface, and the outer skin surface of the patient.

16. The apparatus of claim 14, wherein the electrical impulse is sufficient to inhibit a release of a pro-inflammatory cytokine.

17. The apparatus of claim 16, wherein the pro-inflammatory cytokine is tumor necrosis factor (TNF)-alpha.

18. The apparatus of claim 14, wherein the anti-inflammatory cytokine is transforming growth factor (TGF)-beta.

19. The apparatus of claim 18, wherein the electrical impulse is sufficient to cause at least one of a retinoid or a component of a retinoic acid signaling system to bias a competence of the anti-inflammatory cytokine towards an anti-inflammation.

20. The apparatus of claim 14, wherein the electrical impulse is sufficient to enhance an anti-inflammatory activity of a neurotrophic factor.

21. The apparatus of claim 20, wherein the neurotrophic factor is a member of at least one of a transforming growth factor (TGF)-beta superfamily of neurotrophic factors, a nerve growth factor superfamily of neurotrophic factors, a neurokine superfamily of neurotrophic factors, or an insulin-like family of non-neuronal growth factors.

22. The apparatus of claim 14, wherein the selected nerve is a vagus nerve of the patient.

23. The apparatus of claim 14, wherein the neurodegenerative disorder comprises at least one of Alzheimer's disease, Parkinson's disease, multiple sclerosis, postoperative cognitive dysfunction, or postoperative.

24. The apparatus of claim 14, wherein the electrical impulse is sufficient to modulate the activity of the selected nerve at or near the target region of the patient with decreased measurable pain to the patient.

25. The apparatus of claim 14, wherein the bursts comprise the pulses and at least one of the bursts corresponds to at least one of an up-cycle or a down-cycle of the electrical impulse.

26. The method of claim 14, wherein the electric current is modulated such that the patient has decreased measurable pain.

27. The method of claim 14, wherein the bursts comprise the pulses and at least one of the bursts corresponds to at least one of an up-cycle or a down-cycle of the electrical impulse.

28. A method for treating a neurodegenerative disorder in a patient, the method comprising:

applying an electric current to an outer skin surface of a neck of the patient non-invasively sufficient to transmit the electric current transcutaneously and non-invasively through the outer skin surface of the neck of the patient and generate an electrical impulse at or near a selected nerve within the patient; and modulating the electric current such that the electrical impulse comprises bursts of pulses with each of the bursts comprising a frequency from about 5 Hz to about 100 Hz and with each of the pulses comprising a duration from about 50 microseconds to about 1000 microseconds and such that the electrical impulse is sufficient to increase an activity of an anti-inflammatory cytokine in the patient to inhibit an inflammation and thereby treat the neurodegenerative disorder.

29. The method of claim 28, wherein the electrical current is generated by a power source housed in a housing, wherein the housing hosts a contact surface coupled to the power source, wherein the applying is via the contact surface, wherein the modulating is as the contact surface contacts the outer skin surface.

30. The method of claim 29, wherein the selected nerve is a vagus nerve.

31. The method of claim 30, wherein the housing houses a conduction medium electrically positioned between the power source and the contact surface, wherein the applying is through the conduction medium.

* * * * *